(12) United States Patent
Tearney et al.

(10) Patent No.: US 11,864,743 B2
(45) Date of Patent: *Jan. 9, 2024

(54) APPARATUS, METHOD AND COMPUTER-ACCESSIBLE MEDIUM FOR OBTAINING TISSUE SAMPLES

(71) Applicant: THE GENERAL HOSPITAL CORPORATION, Boston, MA (US)

(72) Inventors: Guillermo J. Tearney, Cambridge, MA (US); Joseph Gardecki, Acton, MA (US); Chia-Pin Liang, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/168,374

(22) Filed: Feb. 5, 2021

(65) Prior Publication Data

US 2021/0401414 A1 Dec. 30, 2021

Related U.S. Application Data

(63) Continuation of application No. 15/557,020, filed as application No. PCT/US2016/021802 on Mar. 10, 2016, now Pat. No. 10,959,712.
(Continued)

(51) Int. Cl.
*A61B 10/04* (2006.01)
*A61B 10/02* (2006.01)
(Continued)

(52) U.S. Cl.
CPC .............. *A61B 10/04* (2013.01); *A61B 1/041* (2013.01); *A61B 5/0066* (2013.01);
(Continued)

(58) Field of Classification Search
CPC ....... A61B 10/04; A61B 1/041; A61B 5/0066; A61B 5/0068; A61B 10/0233; A61N 5/062

See application file for complete search history.

(56) References Cited

U.S. PATENT DOCUMENTS 10,959,712 B2 * 3/2021 Tearney .............. A61B 5/0066
2002/0122246 A1 9/2002 Tearney et al.
(Continued)

FOREIGN PATENT DOCUMENTS

WO 2005047813 A1 5/2005
WO 2008082444 A2 7/2008

OTHER PUBLICATIONS

International Search Report dated May 27, 2016 for International Application No. PCT/US2016/021802 filed on Mar. 10, 2016.
(Continued)

*Primary Examiner* — Joel Lamprecht
(74) *Attorney, Agent, or Firm* — QUARLES & BRADY LLP

(57) ABSTRACT

Apparatus and method can be provided for obtaining at least one anatomical sample. For example, it is possible to provide and insert a housing into a body or provided on a hydrated anatomical structure. Further, with a source, it is possible to emit an electromagnetic radiation which causes at least the anatomical sample(s) to attach to at least one portion of the housing. A compound can be provided on a surface of the housing, and the source provides the radiation to the compound and changes properties thereof to be adhesive. The source can provide the radiation to the housing, and can change properties of a surface thereof to be adhesive. A component can be provided on a surface of the
(Continued)

anatomical structure, and the source provides the radiation to the compound and changes properties thereof to be adhesive.

20 Claims, 37 Drawing Sheets

Related U.S. Application Data

(60) Provisional application No. 62/131,137, filed on Mar. 10, 2015.

(51) Int. Cl.
*A61B 1/04* (2006.01)
*A61B 5/00* (2006.01)
*A61N 5/06* (2006.01)

(52) U.S. Cl.
CPC ........ *A61B 5/0068* (2013.01); *A61B 10/0233* (2013.01); *A61N 5/062* (2013.01)

(56) References Cited

U.S. PATENT DOCUMENTS

| | | |
|---|---|---|
| 2005/0018201 A1 | 1/2005 | de Boer et al. |
| 2005/0272972 A1 | 12/2005 | Iddan |
| 2006/0093276 A1 | 5/2006 | Bouma et al. |
| 2010/0210937 A1 | 8/2010 | Tearney et al. |
| 2013/0267870 A1 | 10/2013 | Lonky |
| 2014/0187999 A1 | 7/2014 | Tearney et al. |

OTHER PUBLICATIONS

International Written Opinion dated May 27, 2016 for International Application No. PCT/US2016/021802 filed on Mar. 10, 2016.

* cited by examiner

FIGURE 1A
FIGURE 1B
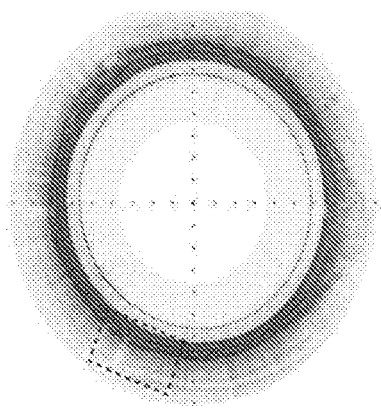
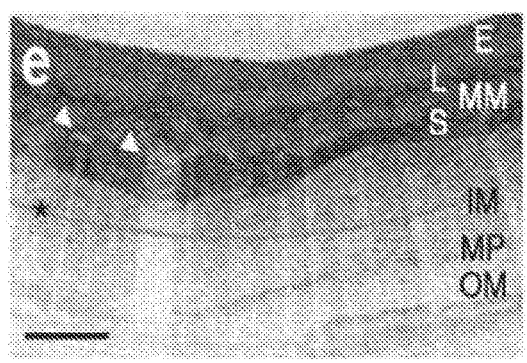
FIGURE 1C

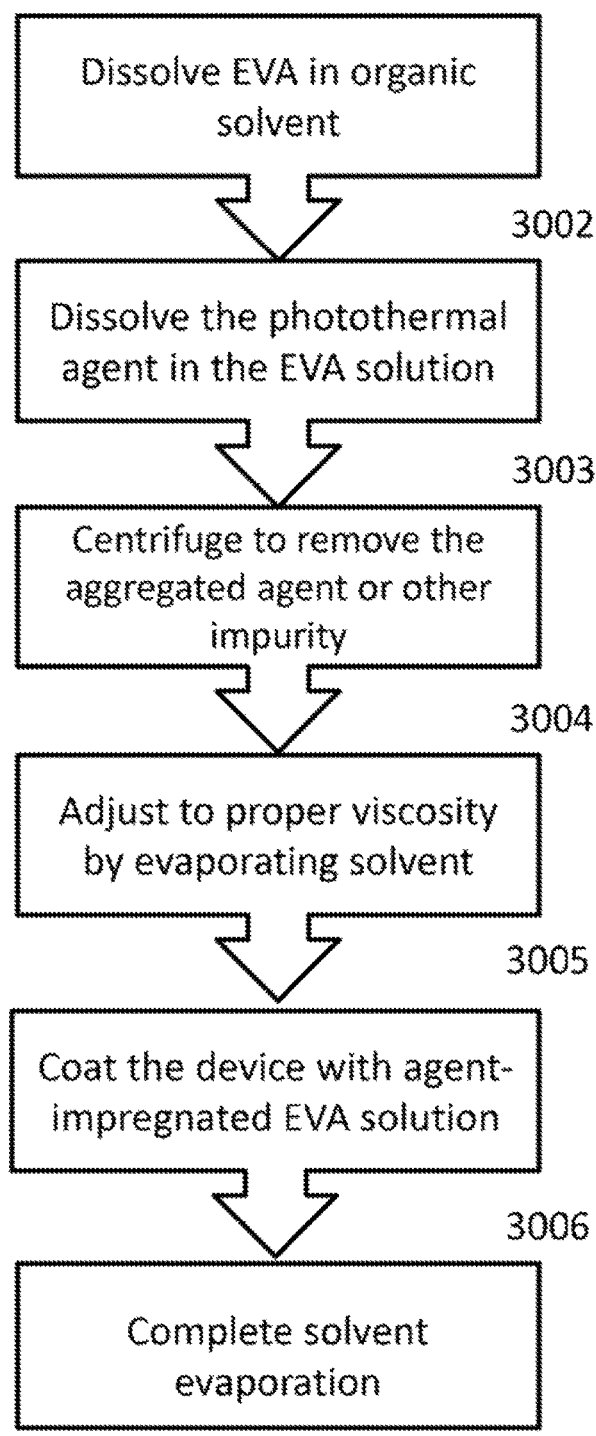
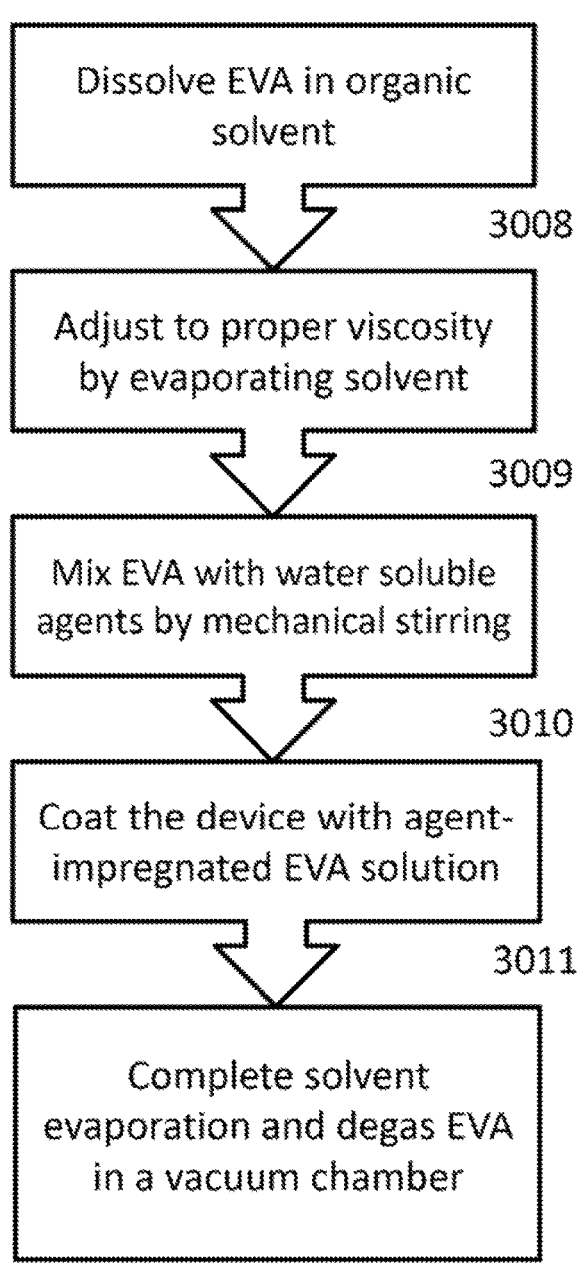

APPARATUS, METHOD AND COMPUTER-ACCESSIBLE MEDIUM FOR OBTAINING TISSUE SAMPLES

CROSS-REFERENCE TO RELATED APPLICATIONS

This application is a continuation of U.S. patent application Ser. No. 15/557,020 filed Sep. 8, 2017 which is a national stage entry of PCT/US2016/021802 filed Mar. 10, 2016 which is based upon and claims the benefit of priority from U.S. Patent Application Ser. No. 62/131,137, filed on Mar. 10, 2015, the entire disclosure of which is incorporated herein by reference.

STATEMENT REGARDING FEDERALLY SPONSORED RESEARCH

This invention was made with government support under EB022077 awarded by the National Institutes of Health. The government has certain rights in the invention.

FIELD OF THE DISCLOSURE

The present disclosure relates to obtaining tissue samples, and more particularly to exemplary methods apparatus and computer-accessible medium for obtaining or otherwise capturing selected tissues in vivo or in situ.

BACKGROUND INFORMATION

In vivo microscopy (IVM) technologies can obtain microscopic images greater than 100 µm resolution and optimally greater than 40 µm resolution are obtained from living tissues. For cellular level resolution, a resolution of greater than 10 µm and greater than 2 µm can be preferred. FIG. 1A shows an exemplary in vivo optical frequency domain imaging (OFDI) acquired from a patient's esophagus. FIG. 1B shows that approximately 30 µm resolution is capable of resolving important structures for disease diagnosis. FIG. 1C shows that spectrally encoded confocal microscopy (SECM) can provide even finer resolution greater than 2 µm capable of visualizing individual cells. In vivo microscopy technologies include optical coherence tomography (OCT), spectral-domain OCT (SD-OCT), swept source OCT (SS-OCT), OFDI, fluorescence microscopy, contact microscopy, oblique backscattering microscopy, confocal microscopy, multi-photon microscopy, SECM, light scattering spectroscopy, and/or the like. In vivo microscopy techniques are sometimes also applied ex vivo to fresh tissues for rapid pathologic assessment. IVM technologies can acquire images that provide structural, functional or molecular information about the sample.

Many of these technologies can be configured so that they obtain microscopic images of the entire organ. In addition, some of these technologies use endoscopic, laparoscopic, gynecologic probes or non-invasive swallowable capsules. It is one goal of IVM to provide a diagnosis of the tissue without its removal. However, many tests that provide vital information may not be obtained by, e.g., IVM or ex vivo application of IVM technologies. Examples of advanced tissue analytic techniques include, e.g., DNA sequencing, 2D-polymerase chain reaction (2D-PCR), RNA sequencing, immunohistochemistry, mass spectrometry (MS), matrix-assisted laser desorption/ionization (MALDI), etc. These additional tests may provide important information that is critical for patient diagnosis. For example, tumors that have similar morphology on histology slides may response very differently to the same treatment. This difference may only be elucidated based on differences in the genome, transcriptome, or proteome. Thus, there can be a need and/or a benefit to utilize such imaging technologies, identify areas of interest, and then extract tissue from these areas of interest for molecular profiling or advanced tissue analytic techniques.

Tissue sampling can be performed under endoscopic guidance or blindly by scraping the tissue surface using a variety of tools such as a speculum, q-tips, or balloon probe for luminal organs. The problem with these methodologies is that a lot of the tissue is not diseased and therefore when the advanced tissue analysis techniques described above are applied, there is substantial noise in the results. Thus, there can be a need and/or a benefit to conduct imaging, identify the diseased tissue, and only extract the diseased tissue for subsequent advanced tissue analytic techniques.

For example, current molecular profiling procedure can include the following steps: patient anesthetization, random or in vivo microscopy guided biopsy, tissue fixing, tissue sectioning, tissue staining, Laser capture micro-dissection (LCM) for isolating the target cells, genomic or proteomic analysis of the target cells. One of the important steps is using LCM for isolating highly pure cell population from heterogeneous tissue. The exemplary components and/or procedures of LCM can include: (i) visualization of the cells of interest via benchtop microscopy (ii) transfer of laser energy to a thermolabile polymer with a formation of polymer-cell composite at the selected area (iii) removal of the target cells from the heterogeneous tissue section. While genomic and proteomic profiling become more and more efficient and economical, the expensive and lengthy process of biopsy and cell isolation is the major roadblock of applying molecular profiling for personalized medicine or disease screening.

IVM techniques can be used to guide excisional biopsy where the images define the area to be excised and a separate instrument is inserted to remove the tissue from the body. This is a cumbersome procedure that can take a lot of time. Thus, there can be a need and/or a benefit to use the same IVM instrument or probe to identify and grab tissue samples while the imaging apparatus is in place. For example, according to one exemplary embodiment of the present disclosure, as described herein below in further detail, when all tissue samples are acquired, the IVM instrument with the tissue can be removed, and then the extracted tissue can be processed via conventional histopathology or advanced tissue analytic techniques.

SUMMARY OF EXEMPLARY EMBODIMENTS

Thus, at least some of the above-described issues and/or deficiencies can be addressed with the exemplary embodiments of the systems, methods and computer-accessible medium according to the present disclosure.

For example, according to one exemplary embodiment of the present disclosure, a microscopic imaging arrangement can be provided which can facilitate a viewing of the tissue at a microscopic level through a light-activated capturing material that is approximately in contact with ex vivo or in vivo hydrated tissue. Photon energy absorbed by light-activated capture material can melt the material and/or triggers photochemical and/or photothermal reaction causing tissue to be incorporated into or stick to the material. This photon energy can be at or near the wavelengths of the imaging light and/or the wavelength can alternatively be different and/or tuned to the light-activated capturing material's absorbance. Moreover, it is possible to utilize a tissue altering light with the capture light to enhance the capture capability by ejecting or cutting tissue. Tissue ejection light can vaporize the water in tissue, and the steam force can eject the tissue.

Tissue cutting light can disconnect the bonds between the target tissue and its surrounding tissues, and thus make the target tissue be easier to be lifted off. When capture light is turned off, the incorporation or binding reaction can stop, and the tissue can become affixed to the capture material, and the bound tissue can be lifted off from surrounding unbound tissue. Depending on the strength of the connection between the bound and unbound tissues, tissue altering light could be applied to facilitate the disconnection. When the connection is weak, capture light by itself and the mechanical force exerted on the capture film can be sufficient to lift off the captured tissue. Further, cells can be extracted from capturing material and processed via advanced tissue, cell, and molecular analysis techniques.

In yet another exemplary embodiment of the present disclosure, it is possible to just utilize a tissue alteration light for capturing tissue. In this exemplary case, the tissue alteration light can be the tissue capture light. The photon energy absorbed by the tissue can generate an explosive water vaporization, which can eject the tissue and melt the adjacent capture material. The ejected tissue can then be fused with the melted capture material.

In yet another exemplary embodiment of the present disclosure, the tissue altering light can increase the temperature in the tissue, and facilitate the photothermal crosslinking between capture material and the tissue. The crosslink can improve the capture efficiency. Capture light and tissue altering light can be used together or independently for achieving the optimal capturing efficiency with minimal system complexity.

Further exemplary apparatus and method according to an exemplary embodiment of the present disclosure can be provided. With such exemplary apparatus and method, it is possible to utilize one optical device to deliver capture/tissue altering light energy to and obtain imaging feedback from within a living person or organism. This exemplary device can contain, e.g., relay optics (fiber based, fiber bundle based, GRIN lens based, free optics based, etc.) that delivers light to other optics (lenses, mirrors, prism, grating, etc.) that can be contained in a housing. The exemplary optical configuration can direct and focus the electromagnetic radiation to the sample and to the capture material to effectuate, e.g., imaging, tissue alterations and/or tissue capture. The beam on the sample can be scanned, e.g., by an actuating configuration in the device such as a driveshaft, distal motors, scanners or the like. The housing of the device can be or include a sheath, balloon, capsule, needle, cannula, catheter and/or the like that is configured to be placed into the body. For tissue capturing, the housing can be coated with a capture material and/or can be made of the capture material. The captured tissue stuck on the housing can be peeled off from the surrounding tissues and/or retrieved from the body when the optical device is removed.

Still further exemplary apparatus and method can be provided according to an exemplary embodiment of the present disclosure. In this exemplary embodiment, capture light, imaging light and/or tissue altering light can be coupled with each other through dichroic couplers. For example, all or most of the light can be coupled into one capture device for delivering the light onto the capturing material and tissue. The back emission light from the tissue can be coupled back into the imaging system and sent to the imaging detector through a coupler. With the imaging feedback, the exemplary system can send capture and change the light energy onto the target tissue when the optical configuration within the probe or scanning apparatus directs the electromagnetic radiation to the target area. Moreover, since the capturing material is coated around or underneath the capture device that transmits the imaging and capture light, the device can provide both imaging and tissue capturing capabilities.

In still another exemplary embodiment of the present disclosure, the exemplary apparatus and method can be used for ex vivo tissue, freshly excised tissues or tissues that are externally accessible. The exemplary optical device can be the same as described above, and it does not have to fit into a housing that is configured to be placed into a living organism. The capture material can be coated around optics or be placed on top of tissue. After the tissue collection, the capture film can be peeled off from tissue by removing the optical device or by mechanical tools, such as tweezers, and/or by other ways. The exemplary imaging apparatus can include a device that can locate the cells of interest and determine whether or not tissue has adhered to the film by observing a change in the optical or physical properties of the film.

In yet another exemplary embodiment of the present disclosure, it is possible to miniaturize the exemplary configuration having the capture light, alteration light, imaging system and scanning unit into a small battery-powered wireless device. The device can transmit the imaging feedback wirelessly to the receiving unit outside the in vivo organism. Based on the imaging feedback, the capture and alteration process can be activated at the selected tissue area through a wireless controller.

In another exemplary tissue capture procedure according to an exemplary embodiment of the present disclosure, the various exemplary devices described herein can be placed to the target area, and in vivo microscopic imaging is performed. With the imaging feedback, the target tissue is identified. After reaching the target area, the capture light is turned on to initiate the incorporation of tissue onto the housing. In vivo microscopy imaging can monitor the process and verify if the suspected tissue is successfully captured. If successful, the capture light will be turned off and the captured tissue will be retrieved with the device. If not, in vivo imaging can be performed again to identify the target tissue and the whole process will be repeated. The captured tissue on the device can be released for advanced tissue analysis. In yet another exemplary embodiment of the present disclosure, it is possible to survey the entire region with comprehensive imaging technique, and then deliver the capture light and/or alteration light to the suspected area for tissue capturing.

In an exemplary mapping procedure according to an exemplary embodiment of the present disclosure, the captured tissue can be associated with its corresponding capture site in the organ. The coordinate of the capture site in organ can be recorded by the position sensor or encoder. The coordinate of the captured tissue relative to the fiducial mark on device can also be recorded. Then, the coordinate of captured tissue on device can be associated with the position of capture sites in organ. After the device is removed from the organ, it is possible to map the position in the organ of each captured tissues by their relative position to the fiducial mark. The coordinate information can be useful for follow-up treatments or correlate information obtained by different tools.

According to yet another exemplary embodiment of the present disclosure, it is possible to coat an imaging capsule with capturing material. For example, after un-anesthetized patient swallows the capsule, the imaging capsule can provide real-time imaging feedback from the patient's gastrointestinal (GI) track. If the suspected area is identified, the capture light can be switched on to capture tissue. After the formation of tissue-capturing material composite, the capsule can be pulled out from patient and the extracted tissue can be used for further analysis. In yet another exemplary embodiment of the present disclosure, the capture light, imaging light, and/or alteration light can be transmitted to the capsule using an optical waveguide or fiber. In a further exemplary embodiment, the fiber can be provided within a tether.

In yet another exemplary embodiment, it is possible to coat an endoscopic balloon with a capture material. In addition or further, the balloon can be configured to contain layers such that the capture film can be melted or thermal cross-linked while the balloon retains its integrity and does not inflate. According to yet a further exemplary embodiment, the balloon can include a thermal insulating layer that protects the air or fluid containing balloon from high temperature that may damage the balloon.

Another exemplary application can include using a coated balloon to capture tissues from blood vessel. For example, the probe can be inserted into the lumen of blood vessel. The balloon can then be inflated. The tissue of interest can be collected after capture light illumination. The balloon can then be deflated and retrieved with the captured tissue. The probe is then retreated into a protective tube to protect the collected tissue from being rubbed off while retrieving the device.

In another exemplary embodiment, it can be important for the optics within the device that is used for delivering the capture, alteration and imaging light to be achromatically corrected. Large achromatic mismatch may cause insufficient power delivery to the capture material or poor imaging resolution. The material with minimum chromatic dispersion can be used or achromatic lens configurations should be used.

According to yet another exemplary embodiment, for maximizing the coupling efficiency of imaging, capturing and alteration light at different wavelength, the coupling optics used in a rotary junction for light beam scanning can be or include achromatic optics.

In one exemplary embodiment, it is possible to coat the capturing material directly on a substrate that comprises the outer housing of the device. The activation light can penetrate through the substrate and be absorbed by the capturing material external to the substrate.

According to still another exemplary embodiment, the apparatus can include an insulation layer or binding layer between the substrate and the capturing material. The insulation layer can prevent the substrate from being damaged by the heat converted from photo energy. If the affinity between the substrate and the capturing material is weak, a binding layer that has good affinity with both substrate and material should be applied. The binding and insulation layer should be approximately transparent to the capture, imaging and alteration light.

In another exemplary embodiment, it is possible to coat the housing by dipping it into a coating solution. According to yet another exemplary embodiment, the coating can be performed with dispense coating. In yet another exemplary embodiment, the coating can be performed with spray coating, spin coating, by melting the capture material surrounding the device, etc.

The capture material can also be used with other medical devices and imaging probes. The capture material can be coated around side-viewing imaging device. The device that delivers the imaging light can also be used for delivering the capturing and/or alteration light. After identifying the tissue that is desired to be captured, the capturing material can be activated to collect the tissue. In a further exemplary embodiment, the optical probe can be configured to be inserted like a needle, catheter, cannular or a sheath, etc. For example, the capture material can be coated in the front of front-viewing imaging device. Again, after suspected tissue is identified, the capture material can be activated to collect the tissue.

In yet another exemplary embodiment of the present disclosure, it is possible to mix ethylene-vinyl acetate (EVA) or chitosan with photothermal agents to create a light-activated capturing material. The agent that can be dissolved in organic solvent can be chemically mixed with EVA. The agent that doesn't dissolve in organic solvent can be mechanically mixed with EVA. Water-soluble agents can also be easily mixed with chitosan.

According to yet a further exemplary embodiment of the present disclosure, a light-activated drug releasing coating can be coated around the housing of an imaging device. The device can perform an in vivo microscopic imaging to identify the tissue of interest. Then, the drug release light can be activated. The ejected drug then can treat local diseased foci. The device can also image and/or treat disease foci with high precision.

To that end, apparatus and method can be provided for obtaining at least one anatomical sample, according to an exemplary embodiment to the present disclosure. For example, it is possible to provide and insert a housing into a body or provided on a hydrated anatomical structure. Further, with a source, it is possible to emit an electromagnetic radiation which causes at least the anatomical sample (s) to attach to at least one portion of the housing. A compound can be provided on a surface of the housing, and the source provides the radiation to the compound and changes properties thereof to be adhesive. The source can provide the radiation to the housing, and can change properties of a surface thereof to be adhesive. A component can be provided on a surface of the anatomical structure, and the source provides the radiation to the compound and changes properties thereof to be adhesive.

In one example, the source can provide the radiation to at least one section of the anatomical sample(s), and can change properties of the section(s) to be adhesive to the portion of the housing or a compound provided thereon. The radiation provided by the source to the at least one anatomical sample can break the bonds of the at least one anatomical sample, can cause the sample to disassociate from an anatomical structure on which it provided, and/or can further causes the disassociated anatomical sample(s) to impact the portion(s) of the housing. The radiation provided by the source can cause a change of temperature, pressure and/or photochemical reaction of the sample(s) or the housing so as to facilitate the attachment of the sample to the housing. In one exemplary implementation, in operation, the housing can be positioned in a close proximity to the anatomical sample(s). The compound can be or can include (i) membrane, (ii) thermo polymer, (iii) hydrogel, (iv) dye-impregnated polymer, and/or (v) optical window.

According to another exemplary embodiment of the present disclosure, an imaging system can be provided which is configure to obtain at least one image of at least one section of the anatomical sample. The imaging system can further facilitate a determination of an area of interest of the section(s) within the image(s). The imaging system can control the source to provide the radiation to the area of interest. The imaging system can include (i) a video imaging arrangement, (ii) an OCT imaging arrangement, (iii) an SECM imaging arrangement, and/or (iv) a confocal imaging arrangement. The imaging system can generate at least one image of the portion(s) of the housing after the source generates the radiation.

In still another exemplary embodiment of the present disclosure, the housing can have a shape of a pill. The housing can be attached to a tether. Alternatively, the housing can be an inflatable balloon.

According to a further exemplary embodiment of the present disclosure, a further source can be provided which is configured to generate at least one further radiation that impacts and (i) cuts at least one section of the at least one anatomical sample, and/or (ii) weakens mechanical bonds that holds the sample(s) to at least one biological structure. The anatomical sample(s) can include a plurality of anatomical samples, and each of the samples can be attached to a different portion of the housing. For example, the image generated by the imaging system can include information regarding the anatomical samples attached to the different portions of the housing. The information can include position data of a location at which each of the structures is attached to the respective portion of the housing. The source can be a pulsed source.

In a still further exemplary embodiment of the present disclosure, the housing can have a structure to prevent a di s-attachment of the sample(s) therefrom. A further housing can also be provided which at least partially covers the portion(s) of the housing when such portion is attached to the anatomical sample(s).

According a another exemplary embodiment of the present disclosure, apparatus and method for releasing at least one compound can be provided. For example, a housing can be inserted into a body, and can be placed substantially adjacent to at least one portion of an anatomical sample. Further, with a source, it is possible to cause an emission of an electromagnetic radiation which causes at least one portion of the housing to release the compound(s) onto the anatomical sample(s).

These and other objects, features, and advantages of the exemplary embodiments of the present disclosure can become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIGS. 1A-1C are exemplary images acquired with the in vivo microscopy devices;

FIGS. 30A and 30B are flow diagrams of exemplary procedures according to exemplary embodiment of the present disclosure for mixing EVA with organic solvent soluble and water soluble photothermal agents;

Figure 2:
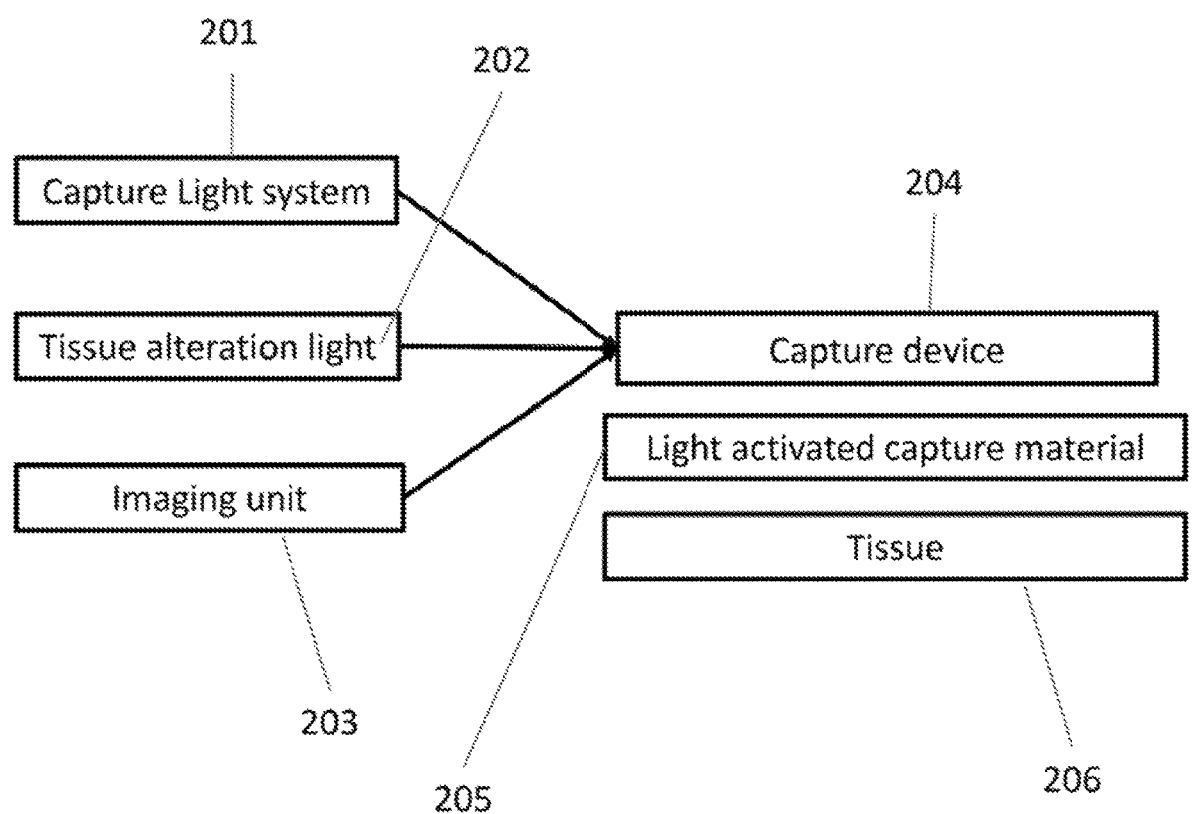
FIG. 2 is a block diagram of an apparatus for imaging and tissue capturing device according to exemplary embodiments of the present disclosure.

Throughout the figures, the same reference numerals and characters, unless otherwise stated, are used to denote like features, elements, components or portions of the illustrated embodiments. It is intended that changes and modifications can be made to the described exemplary embodiments without departing from the true scope and spirit of the subject disclosure. Moreover, while the present disclosure will now be described in detail with references to the figures, it is done so in connection with the illustrative embodiments and is not limited by the particular embodiments illustrated in the figures, or the appended claims.

DETAILED DESCRIPTION OF EXEMPLARY EMBODIMENTS

Various exemplary embodiments of the present disclosure are based on a concept of accurately capturing selected tissue with imaging guidance using one device. The device with both imaging and capturing capabilities, and the corresponding procedures employing the same can significantly reduce the time and cost of tissue collection. Such exemplary device and its corresponding procedure can enhance the imaging of microscopic tissue, the identification of disease, and the capture of the cells of that disease without requiring an additional and possibly more invasive procedure. It is also possible to facilitate—with the exemplary embodiments of the present disclosure—microscopic imaging on fresh or living tissue to select one particular type of tissue, such as tissue containing premalignant or malignant cells, and also capture the tissue that specifically contains a majority of these cells that will enrich and increase the specificity of subsequent advanced tissue and cell genetic, transcriptional, or proteomic analysis.

An exemplary arrangement of components and/or system according to an exemplary embodiment of the present disclosure is illustrated in a block diagram of FIG. 2. For example, light from the capture light system (201) and imaging unit (203) can be coupled into or otherwise provided to a capture device (204) for delivering the photons onto light-activated capture material (205) and tissue (206). The back-emitted signal from the tissue can be coupled back or otherwise provided to the imaging unit (203) for constructing or generating the image. Based on a user determination of the microscopic features of the image that may indicate a certain tissue type, cell type or disease, target tissues can be identified. Then, the device (204) can deliver the capture light (201) through the capture film (205) onto the selected tissues (206).

The device (204) can comprise an exemplary optical configuration, which can include grating, lens, mirror, scanning apparatus, prism, or the like is present at least partially within a housing that on its outer surface contains the capture film (205). This capture material (205) can be a thermoplastic material for example that absorbs capture electromagnetic radiation that is configured to illuminate the film and tissue after an imaging region has been selected for capture. The composite or capture film (205) is configured to be affixed to the outer surface housing and can be removed from fresh or living tissue (206) for further analysis. In one embodiment, the housing of device (204) is made of capture material (205). Alternatively or in addition, the capture film (205) can be removed, as in the case of a scanning apparatus that can scan electromagnetic radiation over the film (205) that is on top of the fresh tissue or external tissue such as skin or tissues exposed by open incision. Not all the capture material (205) would convert the photon energy into heat. For example, some materials form the tissue/material composite by photochemical reaction triggered by the capture light (201).

Besides or in addition to the capturing light (201), it is possible to enhance tissue capturing capability with the tissue alteration light (202), which can eject or cut the tissue. For example, an ejection light (202) vaporizes water to steam, which accumulates in tissue and creates explosive tissue ejection once the steam force over certain threshold. The ejected tissue can be easily collect by the melted capture material (205). Moreover, in certain exemplary cases, the ejection light (202) can work independently, e.g., without the capture light (201). The hot water vapor that ejects the tissue also melts the capture material (205). The melted capture material (205) can then be fused with the ejected tissue. In some other cases, the photo energy that is absorbed by water facilitates the formation of photothermal crosslinks. The functional groups on the capture material (205) can efficiently bind to the functional groups in tissue (206) in an environment with elevated temperature. Photothermal crosslinks can significantly improve the capture efficiency. In yet another exemplary embodiment of the present disclosure, the tissue altering electromagnetic radiation or the ejection light (202) can be applied to the tissue prior to the capture to break tight junctions in the tissue and/or cut the tissue for easier removal following capture by the capture film (205).

Figure 3:
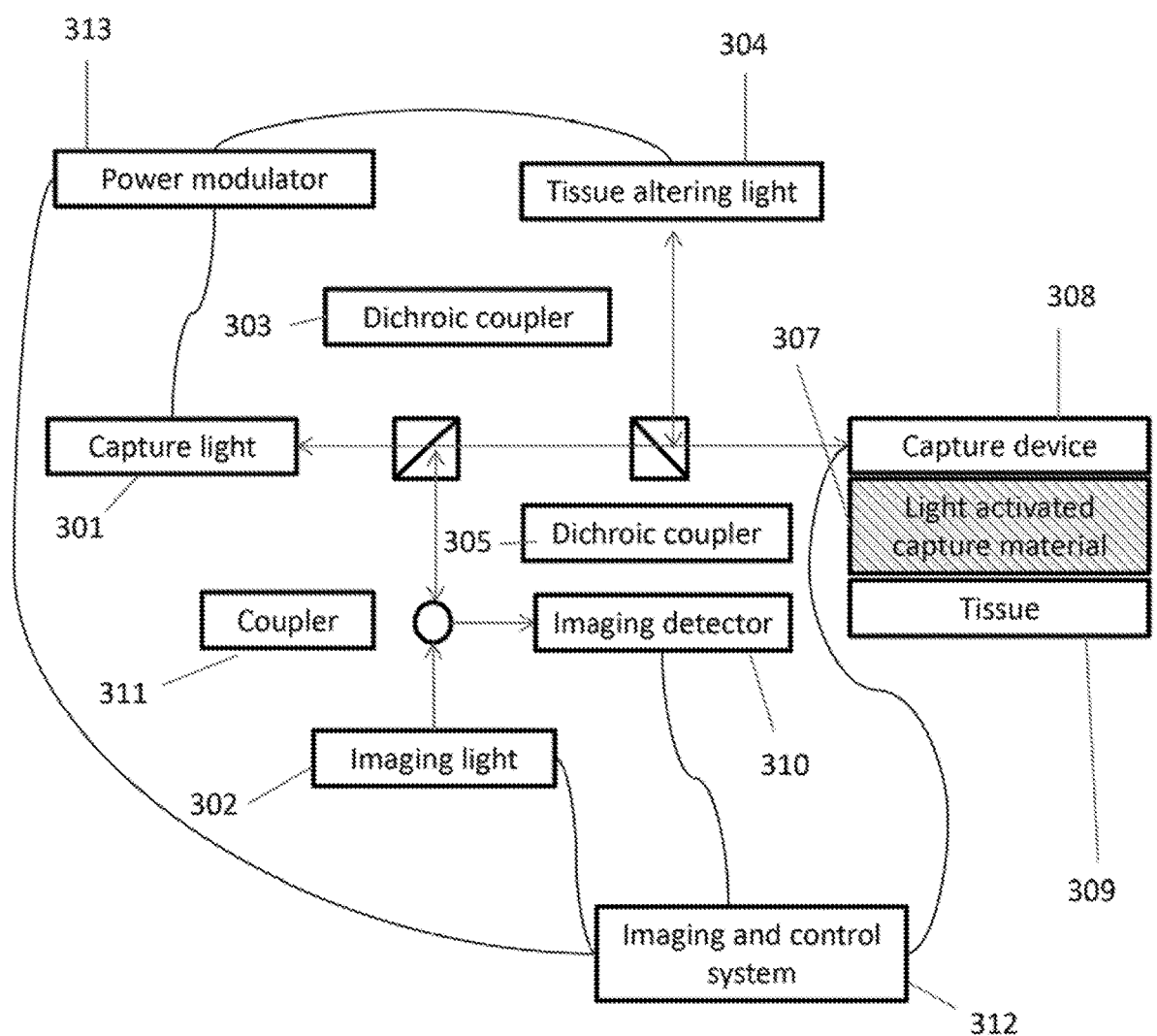
FIG. 3 is a block diagram of the apparatus for imaging and tissue capturing device according to another exemplary embodiment of the present disclosure.

FIG. 3 shows additional details of the exemplary system according to the exemplary embodiment of the present disclosure. For example, a capture light (301) and an imaging light (302) can be coupled by a dichroic coupler (303). A tissue altering light (304) can also be coupled with other light systems with a dichroic coupler (305). If the capture light (301) by itself is sufficient, the tissue altering light (304) can be omitted. If the exemplary system use a hydration-based capturing material (307), which has a high affinity with a dehydrated tissue, the capture light (301) can be omitted. Based on the property of capture material (307), the capture light (301) and the tissue altering light (304) can be used independently and/or together for a beneficial tissue capturing. Light from different system(s) can be coupled into the optical device (308). The optical relay unit in the optical device (308) can be or include, but is not limited to any one or more of, a fiber-based, fiber-bundle based, GRIN optics based, or free space optics based relay unit, etc.

The relay unit can be responsible for delivering the imaging light, capture light, and tissue altering light to other optics which direct the irradiation onto the capture material (307) and tissue (309). A miniaturized device (308) can deliver and/or collect light from a living organism. Light signal from the tissue (309) can be coupled back into an imaging detector (310) through an optical coupler (311). The image can be recorded by an imaging and control system (312) for identifying the tissue and/or area of interest. After the tissue/area of interest is selected, the control system (312) can move irradiation to the target area and switch on the power of alteration light (304) and/or capture light (301) using a power modulator (313) for capturing the selected tissue. The light-activated capturing material (307) coated around the device (308) captures the in-contact and illuminated tissues (309).

Figure 4:
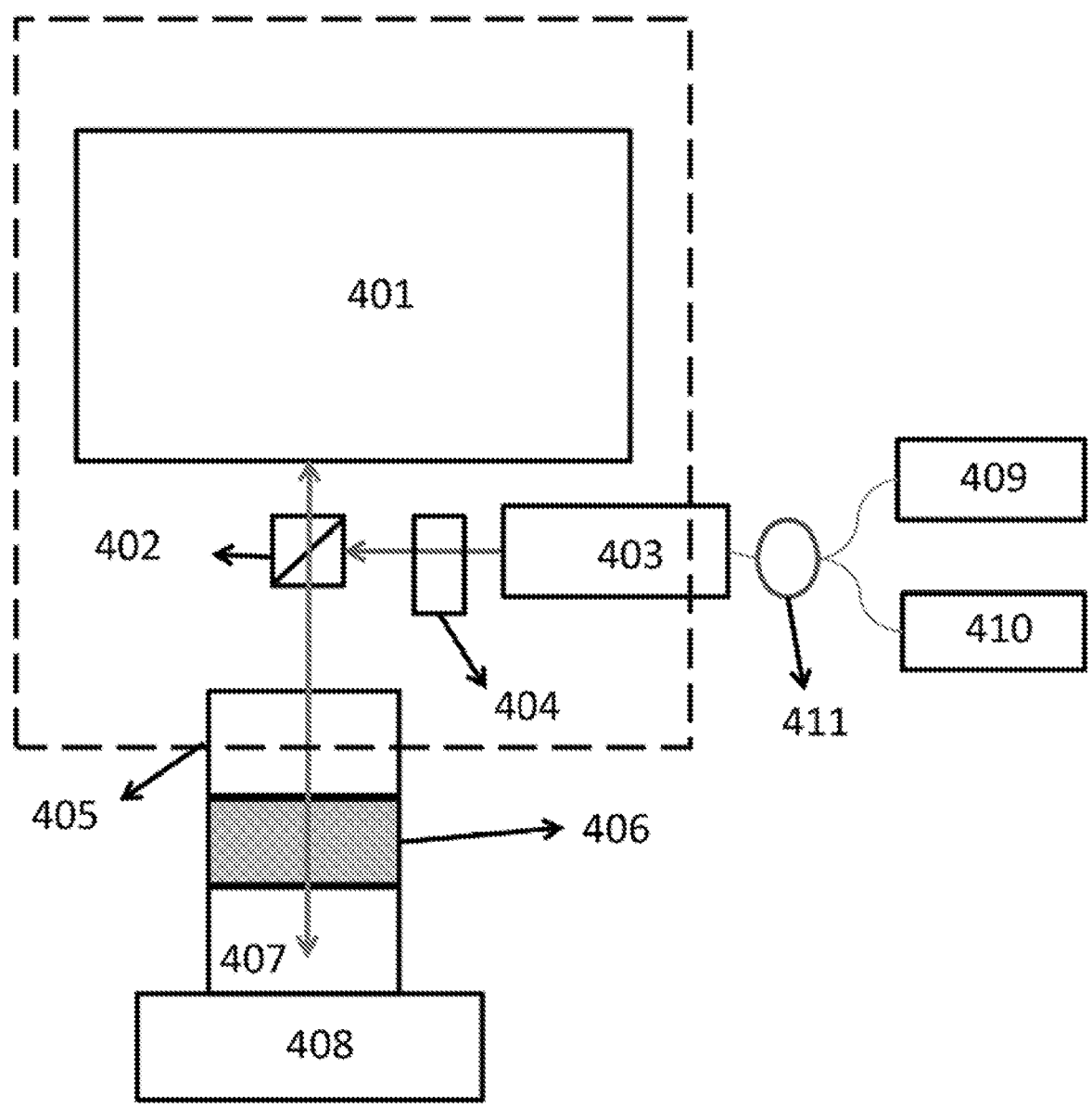
FIG. 4 is a block diagram of the apparatus for imaging and tissue capturing device for externally accessible tissues according to a further exemplary embodiment of the present disclosure.

In yet another exemplary embodiment of the present disclosure, an imaging and capturing system for externally accessible tissue can be provided as illustrated in FIG. 4. For example, a benchtop microscopic imaging system (401) as shown in FIG. 4 can obtain an image from a tissue (407) through an objective lens (405). The exemplary microscopic system can be any benchtop imaging system that is capable of identifying the tissue of interest, such as OCT, optical coherence microscopy, SECM, fluorescence microscopy, confocal microscopy, structured illumination microscopy, super resolution microscopy, etc. A capture material (406) can be placed on top of the tissue for tissue capturing. For example, the capture material (406) can be attached to the objective lens or detached therefrom. After the tissue capture, the capture material (406) can be removed by mechanical tool, such as a tweezers.

The capture light (409) and/or tissue altering light (410) can be coupled with each other by a coupler (411), and then be coupled into or otherwise provided to the miscopy imaging system through a connector (403) and a dichroic coupler (402). The input connector (403) could be, but is not limited to, a fiber optics connector with collimator. The dichroic coupler (402) can couple the imaging light and capture/tissue altering light. The capture/tissue altering light energy can be focused on the sample (407) by the objective lens (405). After the imaging identification, the spot can be scanned on selected area either by a scanner in optical path (404) or a motorized stage (408) holding the sample (407). After the tissue capture, the composite can be lifted off or otherwise removed by separating the objective lens (405) and the tissue (407) (e.g., if capture film is attached on the objective lens) and/or by an external mechanical force.

Figure 5:
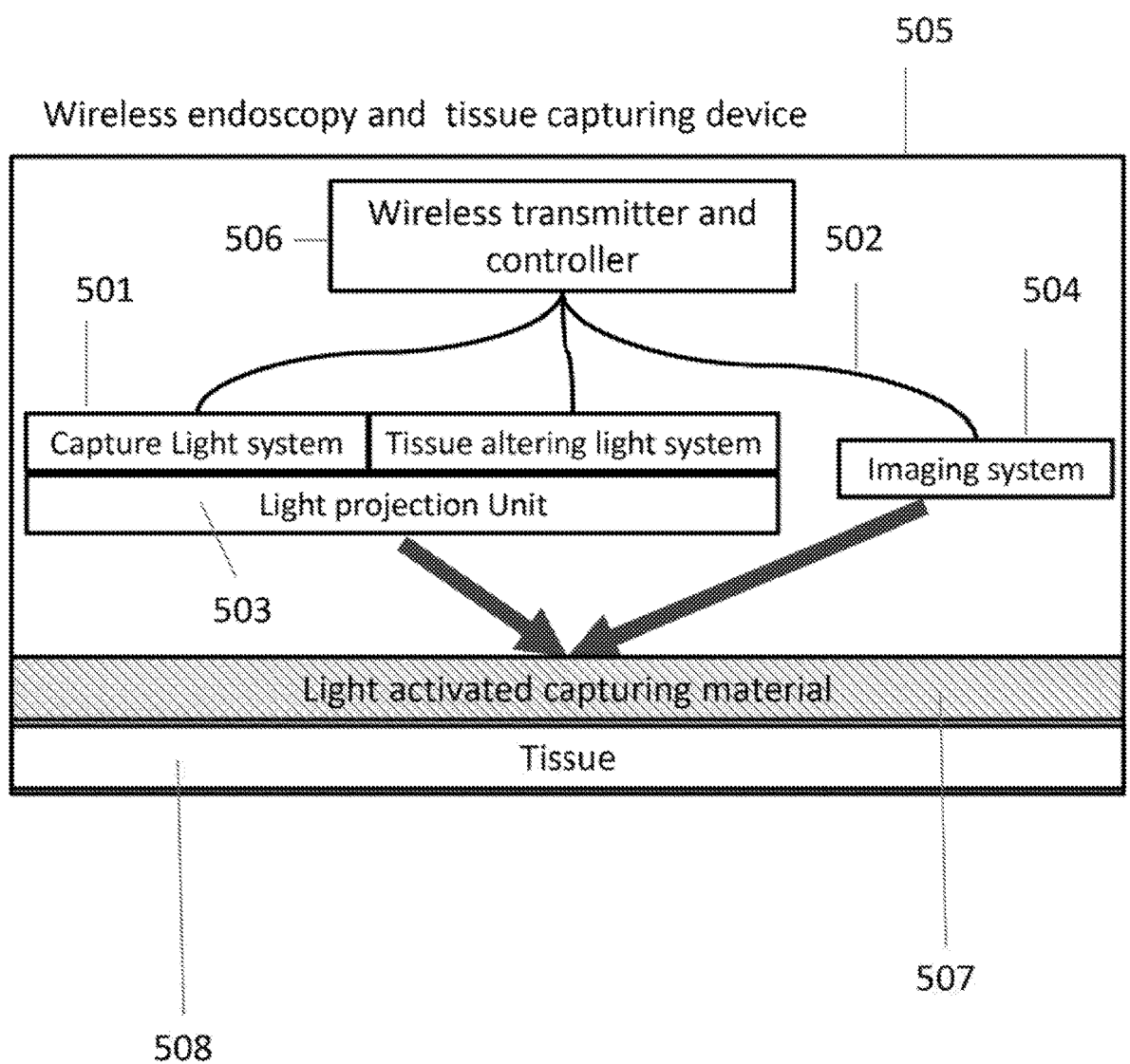
FIG. 5 is a block diagram of the apparatus for wireless imaging and tissue capturing device according to yet another exemplary embodiment of the present disclosure.

In yet another exemplary embodiment of the present disclosure, as shown in FIG. 5, it is possible to miniaturize or otherwise reduce a capture light system (501), a tissue altering light system (502), a light projection unit (503) and an imaging system (504) into a compact and wireless device (505). For example, a wireless transmitter and controller (506) can transmit the acquired image wirelessly to a remote receiver for identifying and selecting the tissue of interest. The wireless controller (506) can control the projection unit (503) to transmit a capture and alteration light onto the selected area. A light-activated capturing material (507) coated around the device can capture the target tissue (508), which can be retrieved with the wireless device (505).

Figure 6:
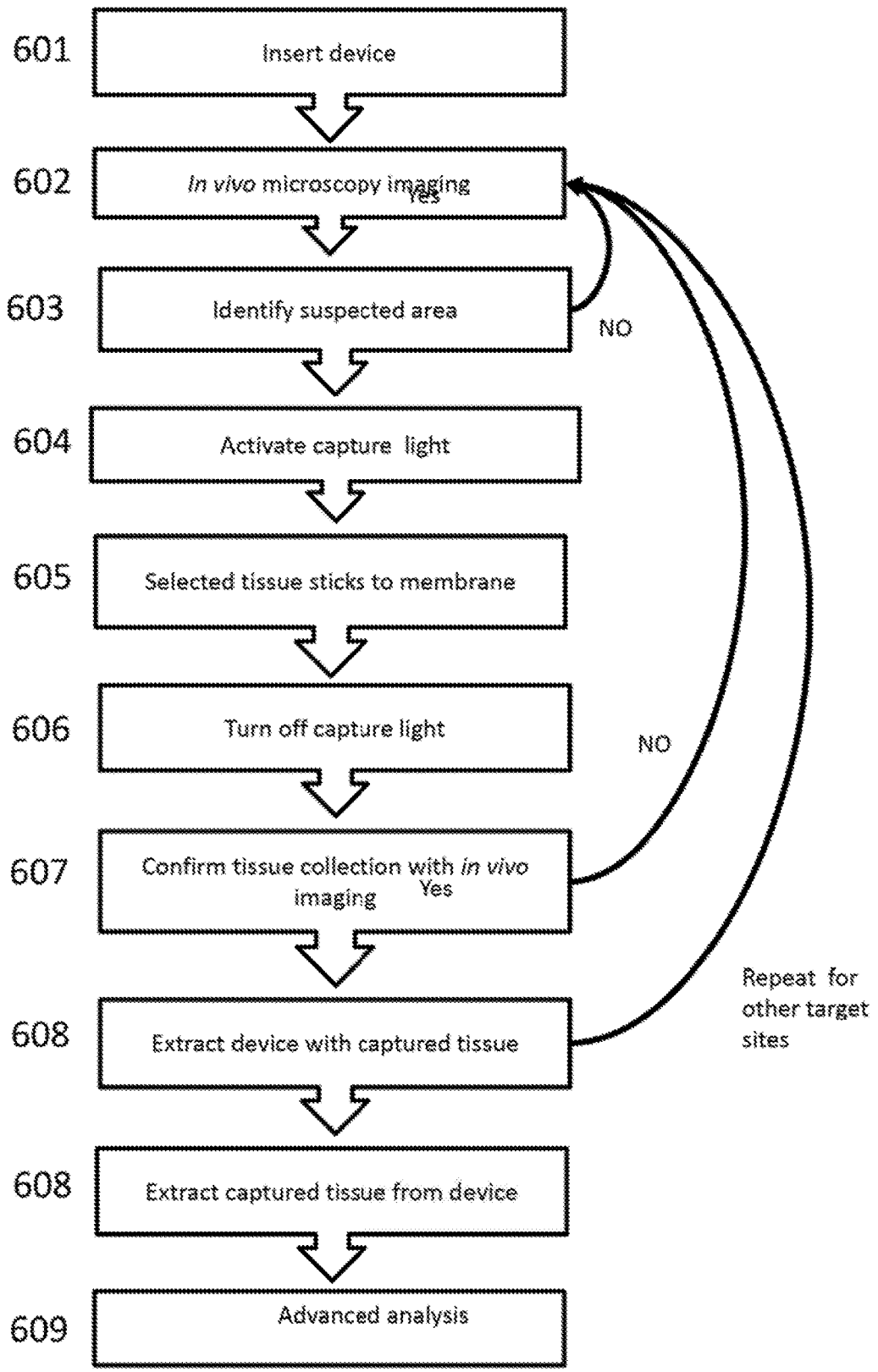
FIG. 6 is a flow diagram of a tissue capturing procedure with real-time imaging according to an exemplary embodiment of the present disclosure

FIG. 6 shows the flow diagram of a procedure for imaging and capturing tissue with one device, according to an exemplary embodiment of the present disclosure. Initially, e.g., the device can be placed into the position to start the imaging (step 601). The suspected tissue can be identified (step 603) in real time using in vivo microscopic imaging (step 602). If no suspected tissue is identified, the device can be repositioned or will travel to another location in the body or another area on the tissue. While the suspected tissue appears in the real-time imaging, the capture light can be switched on, and delivered to the suspected tissue through the same optical device (step 604). Alternatively, a second optical configuration could be utilized to deliver the capture light. The tissue alteration light, where the characteristics of tissue altering include, breakage of tight junctions, ablation, cutting, marking, separation from another tissue type, or the like, can be switched on before, after, or simultaneously with the capture light to enhance the tissue collection. The tissue alteration light can also be used an independent tissue capture light.

After receiving the photon energy from capture light, light-activated capturing material surrounding the device is infused or cross-linked with tissue (step 605). After delivering sufficient power for tissue capturing, capture light and tissue alteration light can be turned off (step 606). In one exemplary embodiment, imaging the capture film after tissue capturing can confirm whether the tissue collection is successful (607). If successful, the device with the capture tissue can be retrieved (step 608) and the tissue stuck on the film can be extracted (step 609) for further analysis (step 610). If suspected tissue is not collected, the exemplary procedure can be repeated. Alternatively, a different region on the housing of the device that contains a different region of the capture film that has not yet been activated or affixed to tissue may be positioned to another area of the tissue and the procedure may be repeated.

Figure 7:
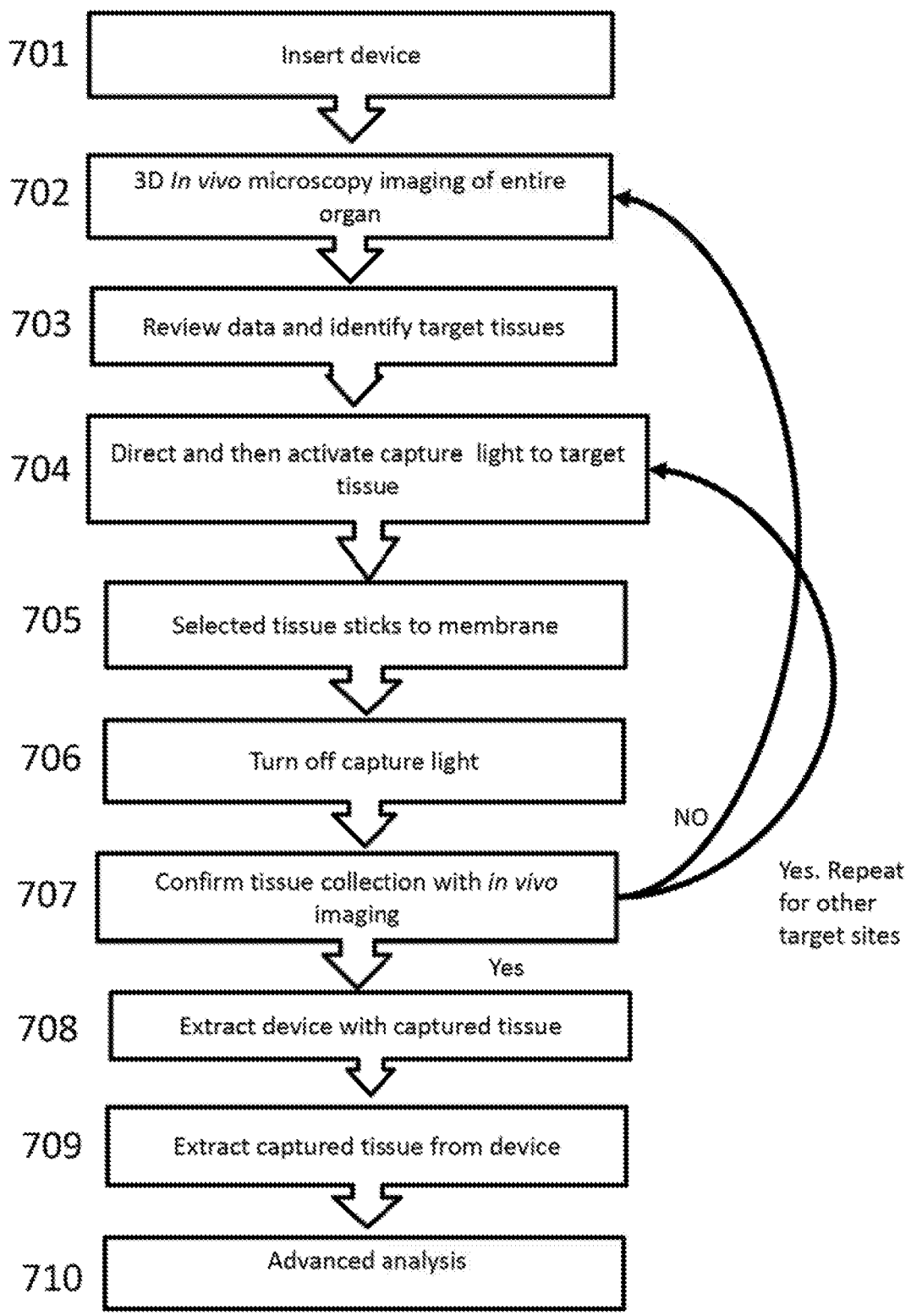
FIG. 7 is a flow diagram of the tissue capturing with comprehensive imaging according to an exemplary embodiment of the present disclosure.

In yet another exemplary procedure, a comprehensive image can be obtained first, then the tissue capturing is performed on specific regions based on the comprehensive image, as shown in a block diagram of FIG. 7. For example, in the beginning, the imaging device coated with light-activated capturing material is placed into position (step 701). A 3D comprehensive in vivo image can be acquired by the device (step 702). The image can be reviewed and suspected tissues are identified (step 703). The optics within the imaging device can be configured to guide the capture and/or tissue altering radiation to the selected area (step 704). The selected tissue is attached on the device (step 705). When the capture is finished, the capture and/or tissue altering radiation is turned off (step 706). In one exemplary embodiment, imaging the capture film after tissue capturing can confirm whether the tissue collection is successful (step 707). If successful, the device with the capture tissue can be retrieved (step 708) and the tissue stuck on the film can be extracted (step 709) for further analysis (step 710). If suspected tissue is not collected, the procedure can be repeated. Alternatively, a different region on the housing of the device that contains a different region of the capture film that has not yet been activated or affixed to tissue may be positioned to another area of the tissue and the procedure may be repeated.

Figure 8:
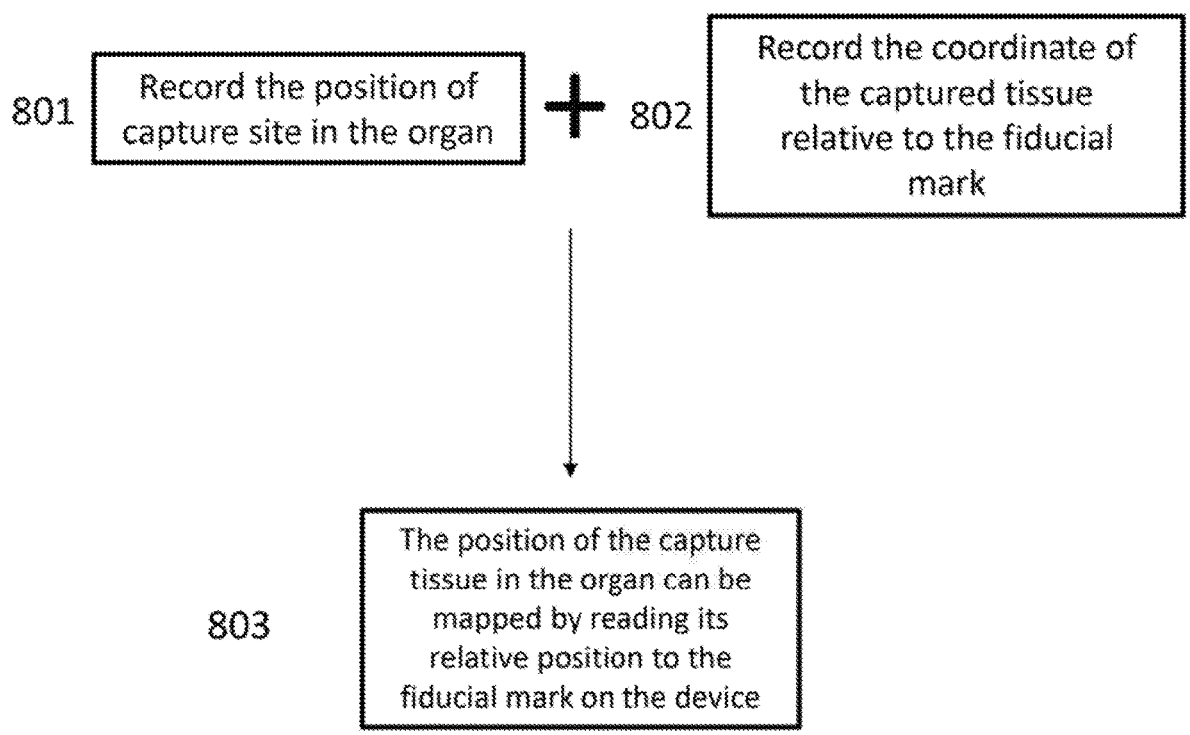
FIG. 8 is a flow diagram of a mapping procedure for capturing the tissues on device to the capture sites in organ according to an exemplary embodiment of the present disclosure.

FIG. 8 shows a block diagram of an exemplary procedure of tissue mapping according to an exemplary embodiment of the present disclosure. For example, the position of capture site in organ can be recorded (step 801) by the position sensor or the encoder in the device. In image, the relative position between fiducial mark and the captured tissue can also be recorded (step 802). The coordinate of the captured tissue on the device can be correlated with the coordinate in the organ (step 803). The information can facilitate mapping of the information extracted from the captured tissue to a specific location in organ.

Figure 9:
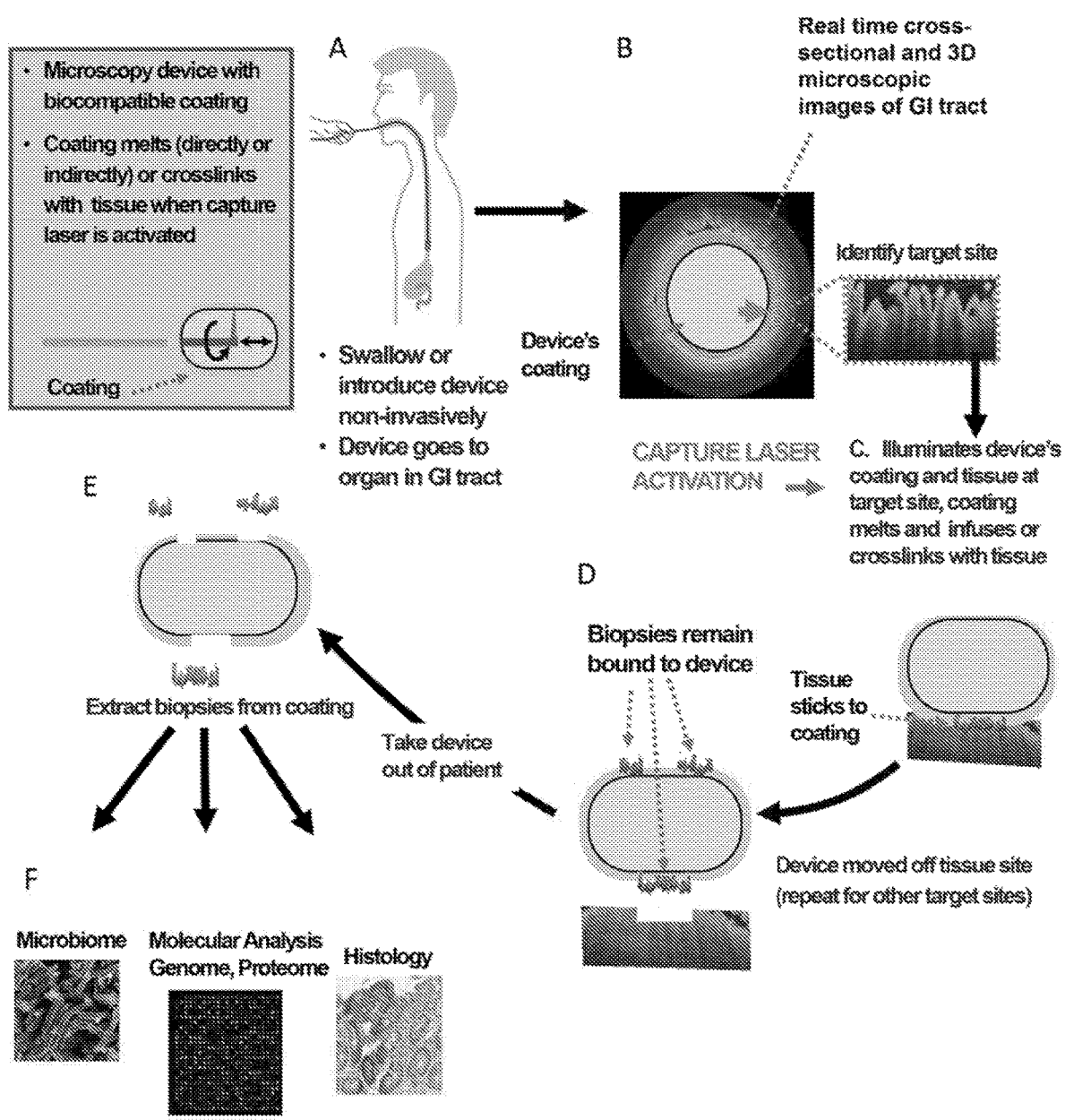
FIG. 9 is a flow diagram of the tissue capturing procedure with real-time imaging in gastrointestinal track according to an exemplary embodiment of the present disclosure.

FIG. 9 shows an exemplary procedure for tissue capturing with real time imaging in GI track. For example, in portion 9A, patient swallows the device with a capture coating on the outer surface. In portion 9B, the device identifies the microscopic aberrant tissues. In portion 9C, it is possible to activate and project the capture laser on target tissue to integrate the tissue with capture coating. In portion 9D, it is possible to turn off the capture laser to stop capturing and move the device to dissociated the captured tissue from its surrounding tissues. Repeat the procedure for other target sites. In portion 9E, it is possible to extract the tissue attached on the capture coating for downstream molecular analysis. In portion 9F, it is possible to perform an advanced tissue analysis.

Figure 10A:
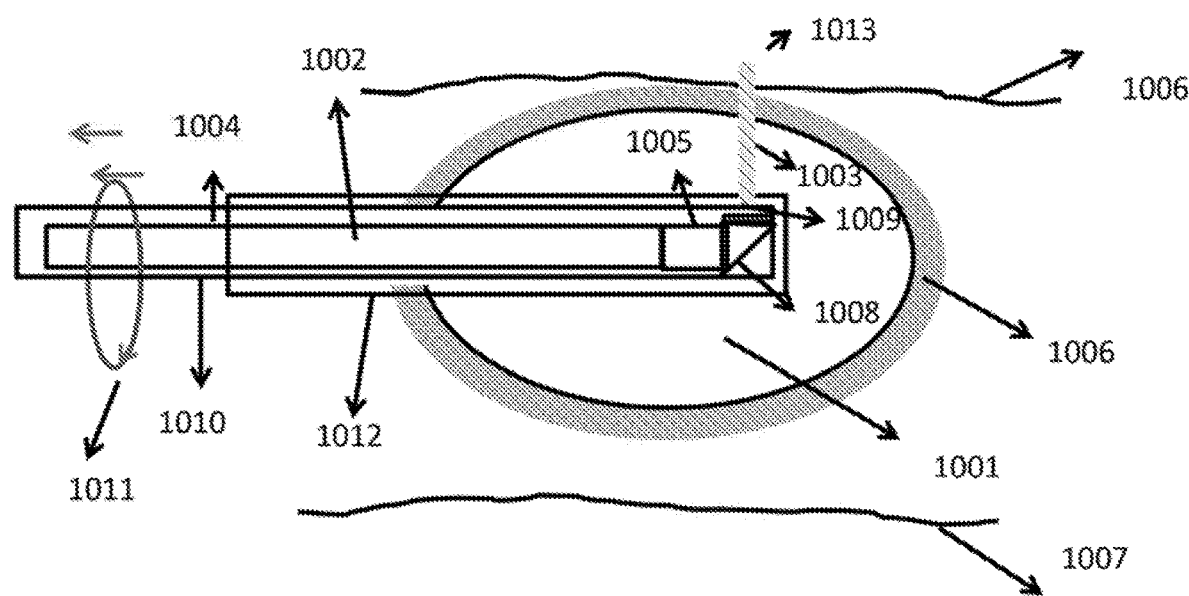
FIG. 10A is a cross-sectional view of an exemplary arrangement of a tethered capsule, according to an exemplary embodiment of the present disclosure, within an organ for the purpose of imaging and tissue capturing.
Figure 10B:
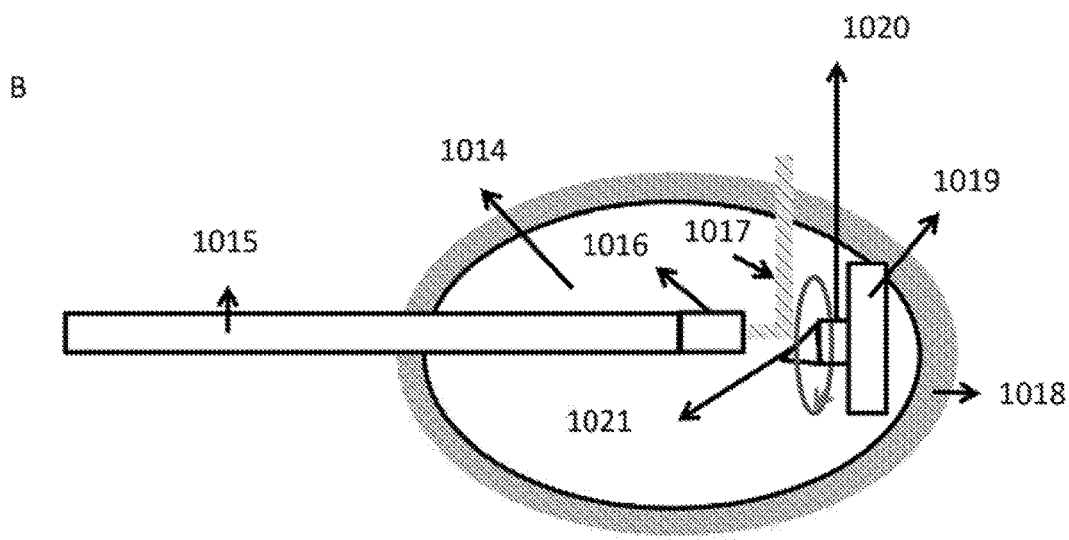
FIG. 10B is a cross-sectional view of another exemplary arrangement of the tethered capsule, according to a further exemplary embodiment of the present disclosure within the organ for the purpose of imaging and tissue capturing.

In an exemplary embodiment of the present disclosure, the capture material can be coated around a tethered capsule endomicroscopic device, as shown in FIGS. 10A and 10B. Such device can be a swallowable capsule that can be attached to a tether that contains an optical fiber or additionally a driveshaft that rotates the optical fiber and the optics within the capsule. Alternatively, the capsule can contain a motor that rotates the optics and/or the fiber. FIG. 10A shows a capsule (1001) and a tether (1002) connected to it. The capsule (1001) can be easily swallowed by an unsedated patient to acquire high resolution images from internal tissues such as gastrointestinal (GI) tract. After imaging, the identification of the tissue/area of interest, and tissue capture, the capsule and captured tissue can be retrieved by pulling the tether (1002). FIG. 10A shows details of the exemplary capsule device. This exemplary device can image and capture tissue. The imaging light, capture light and/or tissue altering light (1003) can be delivered into the capsule (1001) using, e.g., a relay optics (1004), which can be or include, but is not limited to, optical fiber, grin lens, reflector, prism, mirror or fiber bundle, etc. The focusing optics (1005) can be or include, but is not limited to, lens, gradient refractive (GRIN) lens, ball lens, lens assembly, etc., focus light onto a capturing film (1005) or the tissue (1006, 1007). Since the tissue (1006, 1007) surrounds the device, the light can be deflected to the side by a reflective surface (1008).

Before light exits the capsule (1001), in one exemplary embodiment, it can be transmitted through astigmatism correction and/or achromatic optics (1009) for correcting the aberration caused by asymmetrical geometry of the capsule (1001) or other optical interfaces or elements in the optical configuration. In this exemplary embodiment, the optics are associated with a drive shaft (1010), which allows the light beam (1003) to be scanned at least one of circumferentially or linearly (1011). In yet another exemplary embodiment, the beam can be scanned in a manner such that a 2D or 3D image of a large portion of the organ such as a luminal organ is imaged. A protective sheath (1012) outside the drive shaft can prevent tissue from being damaged by the motion of drive shaft (1010) Such exemplary drive shaft (1010), relay optics (1004), outer sheath (1002) assembly is termed a tether.

Following the procedures described herein above and shown in FIGS. 6 and/or 7, the capture light and/or tissue altering light can be switched on when the light beam (1003) irradiates target tissue(s). After receiving the light energy, the selected tissue (1013) can be affixed to the material (1006), which is affixed to the capsule (1001). After imaging and capturing, which can take place at multiple locations in the tissue and at different regions on the capsule, the entire capsule (1001) can be removed from the organ by pulling the tether (1002). The tissue that is retrieved with capsule can be extracted from the capsule for further analysis. Each tissue region on the capsule may additionally be associated with the in vivo microscopy image that was used to target that specific region. FIG. 10B shows exemplary details of the capsule with distal motor for beam scanning. The light (1017) transmitted by the relay optics (1015) can be focused by focused optics (1016), and deflected by a reflective surface (1021) to the tissue and captured coating (1018) surrounding the capsule (1014). A distal motor (1020) that is affixed inside the capsule through a holder (1019) can be used to rotate the reflective surface (1021) and/or perform the circumferential scan.

Figure 11:
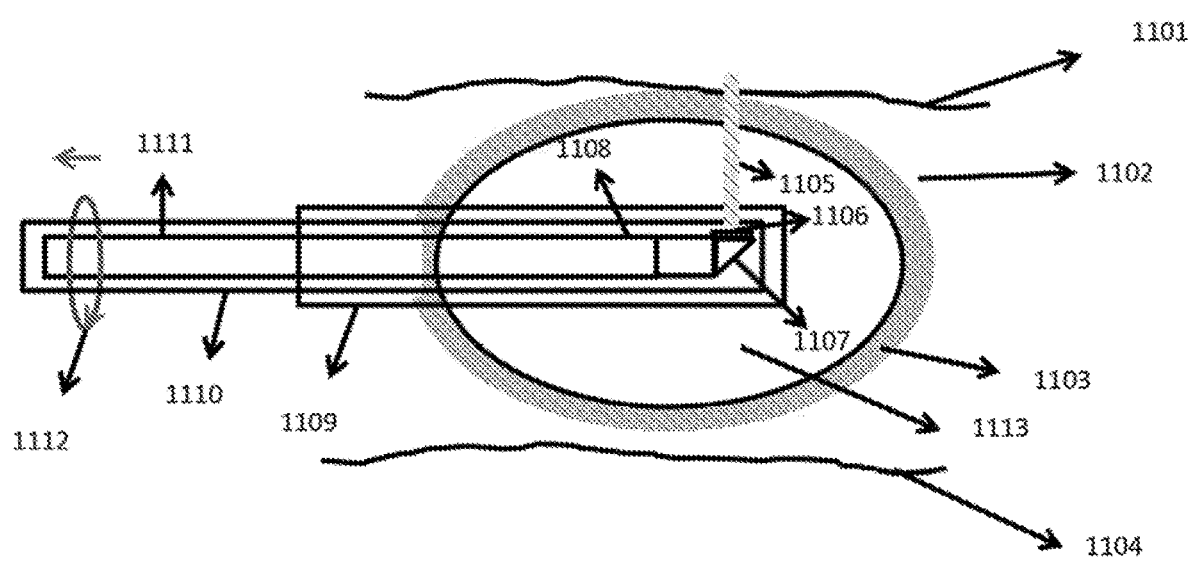
FIG. 11 is a cross-sectional view of an exemplary arrangement of a balloon device, according to an exemplary embodiment of the present disclosure, within the organ for the purpose of imaging and tissue capturing.

In yet another exemplary embodiment of the present disclosure, it is possible to coat the capture material or film around a balloon (1113) as shown in FIG. 11. The optical components of the balloon endoscopy may be similar with the capsule endoscopy (shown in FIG. 10) or alternatively the optical components can comprise other exemplary optical configurations such as SECM or scanning microscopy configurations. Balloon endoscopy configuration can comprise an optical configuration that can include relay optics (1111) to deliver imaging, capture and alteration light. After the relay optics (1111), the optics configuration can further include focusing optics (1108) which can focus light to a small spot. In one exemplary embodiment, the balloon (1113) can be inserted into the body and inflated so that tissue (1101, 1104) is surrounding the device. A reflective element (1107) such as a mirror, prism, or grating etc., can deflect light beam (1105) to the side of balloon (1113) on a portion of the tissue to facilitate the electromagnetic radiation to impinge upon the surrounding tissue (1101, 1104). Before light exits the balloon (1113), it may also pass through an astigmatism correction optics (1106) for correcting the aberration caused by the asymmetrical geometry of components within the balloon device (913).

The entire optics can be associated with a drive shaft (1110), which can facilitate the light beam (1105) to be scanned at least one of circumferentially and linearly (1112) for constructing a 2D or 3D image. In one embodiment, a protective sheath (1109) outside the drive shaft prevents tissue from being damaged by the motion of drive shaft (1110). Following the procedures described herein above with reference to FIG. 6 or 7, at least one of capture light or tissue altering light is switched on when the light beam (1105) can irradiate the target regions within the tissues, as determined by the in vivo microscopy image. After receiving the light energy, a characteristic (such as, e.g., the temperature of the capture material (1103)) can cause a change in the capture material such that it becomes associated with the target tissue and affixes the selected tissue with the capture film on the balloon (1113).

Figure 12:
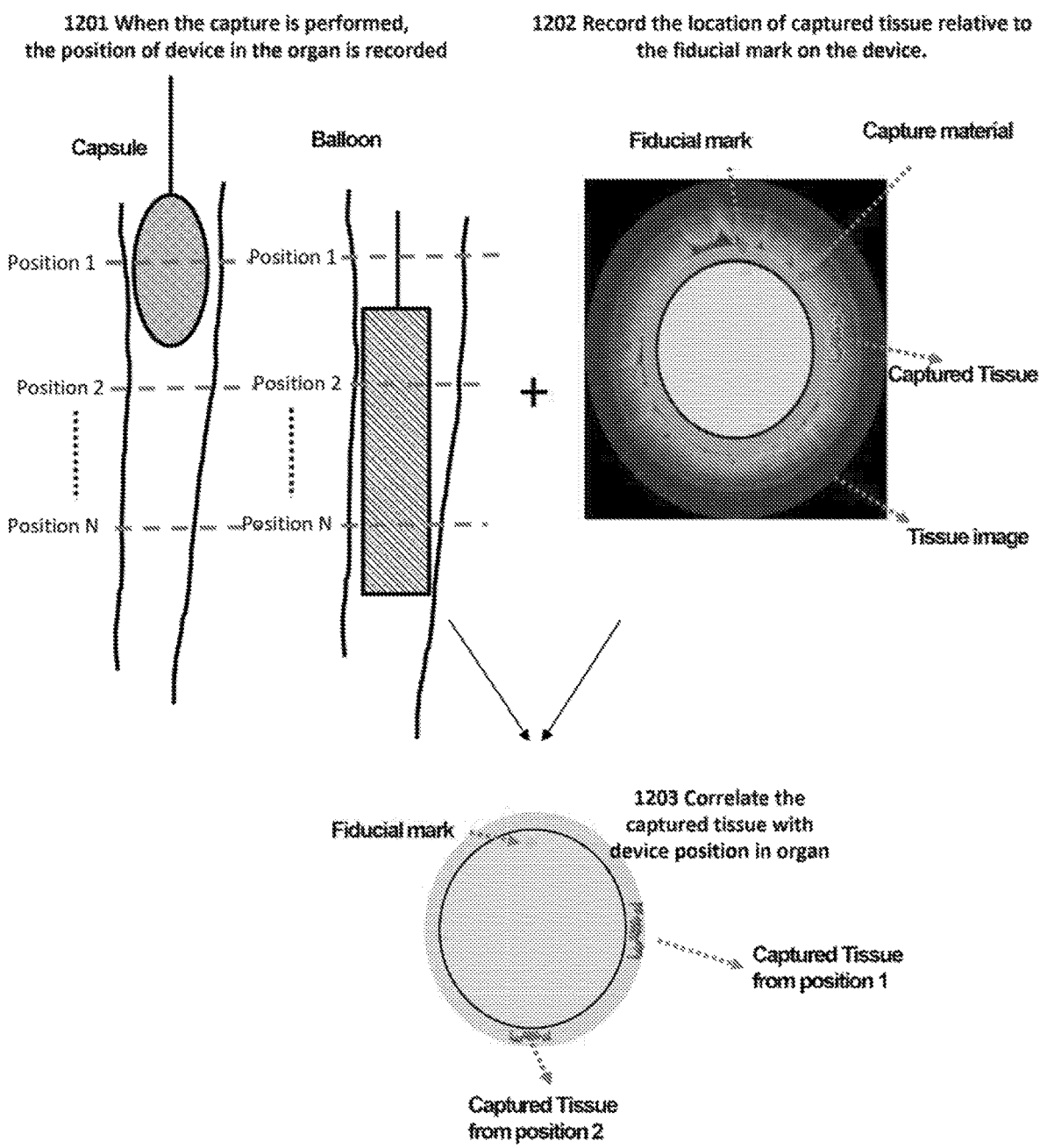
FIG. 12 is a procedure flow diagram of mapping the capture tissues on capsule or balloon to the capture sites in organ according to an exemplary embodiment of the present disclosure.

FIG. 12 shows an exemplary procedure of tissue mapping using capsule or balloon according to an exemplary embodiment of the present disclosure. For example, the position of capture site in organ can be recorded (1201) by the position sensor in capsule or the encoders in the proximal motors in the balloon system. In image, the relative position between fiducial mark and the captured tissue can also be recorded (1202). The coordinate of the captured tissue on the device can be correlated with the coordinate in the organ (1203). The information can facilitate a mapping of the information extracted from the captured tissue to a specific location in organ.

Figure 13A:
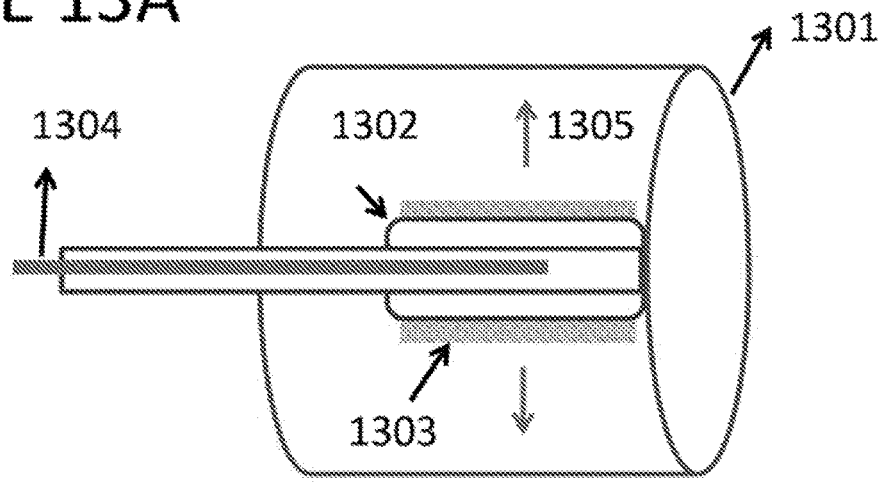
FIGS. 13A-13C are cross-section views of the exemplary device performing tissue capturing with real-time imaging in blood vessel using a balloon catheter according to an exemplary embodiment of the present disclosure.
Figure 13B:
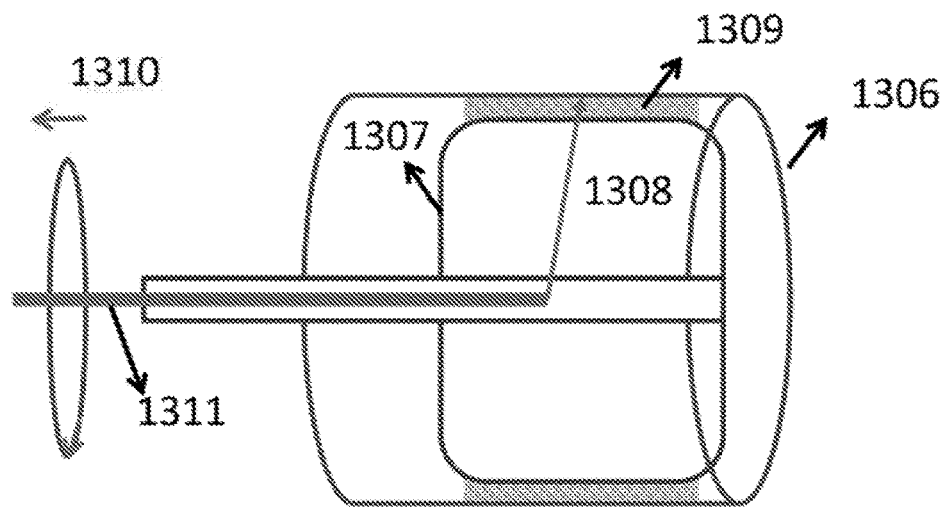
Figure 13C:
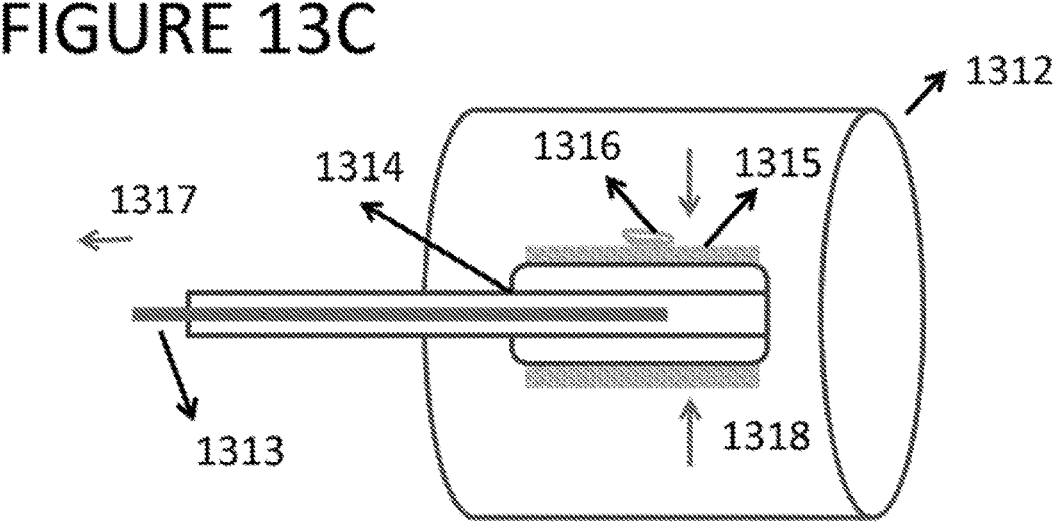

One exemplary application can be or include using a coated balloon to capture tissues from blood vessels. FIG. 13 shows exemplary steps of this exemplary procedure. For example, in the first step (shown in FIG. 13A), a deflated balloon catheter (1302) with light-activated coating (1303) and optical probe (1304) can thread through the lumen of blood vessels (1301) to reach the region of interest. After reaching the target site, the balloon can be inflated (1305). The inflated balloon (1307) can ensure that the coating (1309) has good contact with the vessel wall (1306) (see FIG. 13B). The capture light (1308) can activate tissue capturing at the illuminated sites. The optical probe (1311) can be scanned circumferentially and pulled back (1310) to cover the region of interest. After tissue-coating composite is formed, the balloon can be deflated (1318) (see FIG. 13C). The tissue (1316) that is attached on the coating (1315) can be torn off or otherwise removed from the vessel wall (1312), and retrieved (1317) with balloon catheter (1314) and optical probe (1313) for further analysis.

Figure 14:
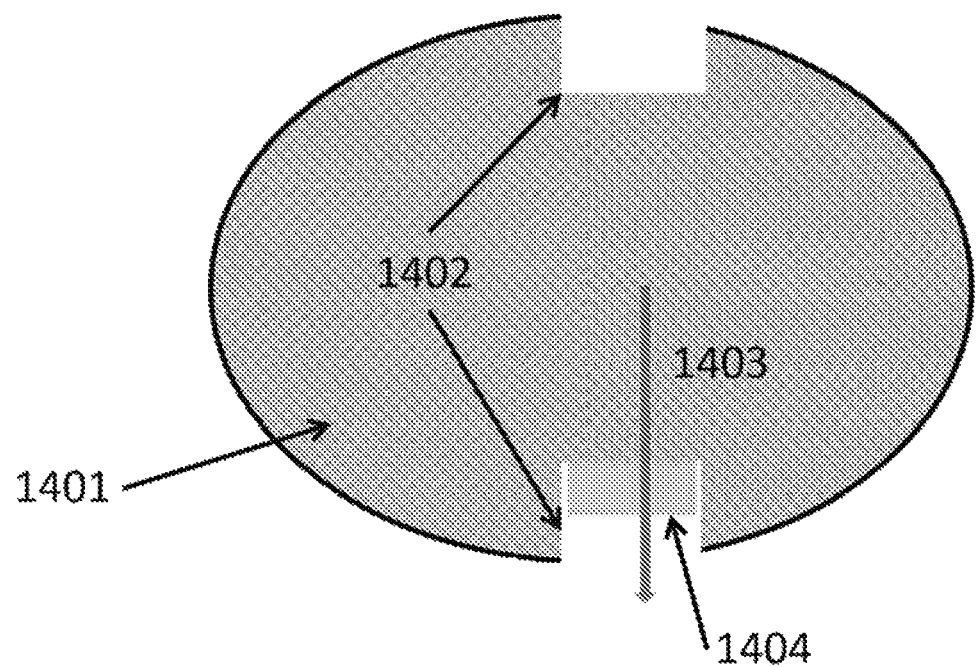
FIG. 14 is a side cross-sectional view of an exemplary arrangement of a tethered capsule with special housing structure, according to an exemplary embodiment of the present disclosure, for protecting the captured tissue.

In one exemplary embodiment, the tissue can be ejected by explosive vaporization and is captured at some distance away from the tissue surface. In this case, the housing can be configured so that the captured tissue can be well protected while moving the device (see FIG. 14). For example, a dent (1402) can be created on the housing, which is coated with capture material (1401). The light (1403) that illuminates the dented space can eject the tissue (1404) into the dented space. This exemplary configuration can significantly reduce the shear force applied on the captured tissue (1404) while moving the device.

Figure 15:
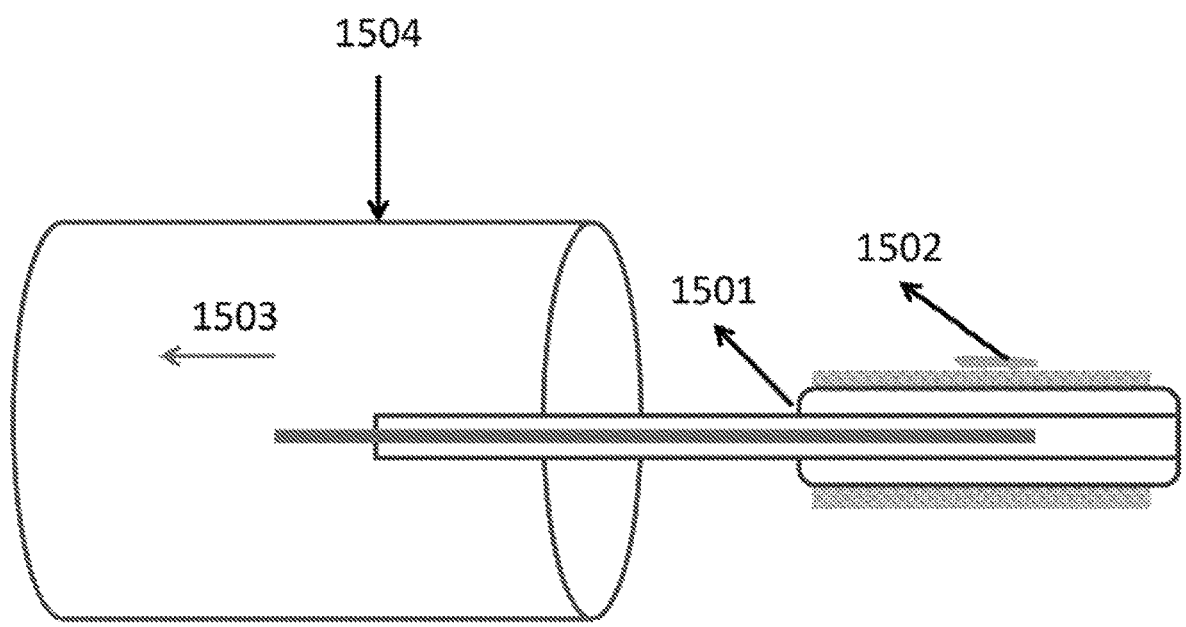
FIG. 15 is a cross-sectional view of another exemplary arrangement of a balloon with an outer housing, according to an exemplary embodiment of the present disclosure, for protecting the captured tissue.

In yet another exemplary embodiment, shown in FIG. 15, the captured tissue (1502) on a deflated balloon probe can be protected by retreating the device (1503) into a protective sheath (1504). This exemplary configuration can prevent or otherwise reduce tissue loss while moving the device inside tissue lumen.

Figure 16A:
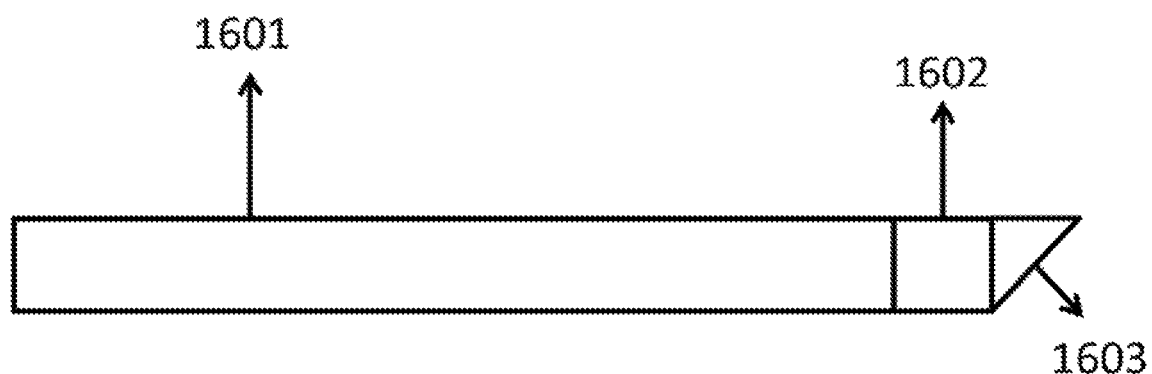
FIGS. 16A and 16B are cross-sectional side views of an exemplary arrangement of achromatic optical probes, according to an exemplary embodiment of the present disclosure, for focusing light at different wavelength to a proper position.
Figure 16B:
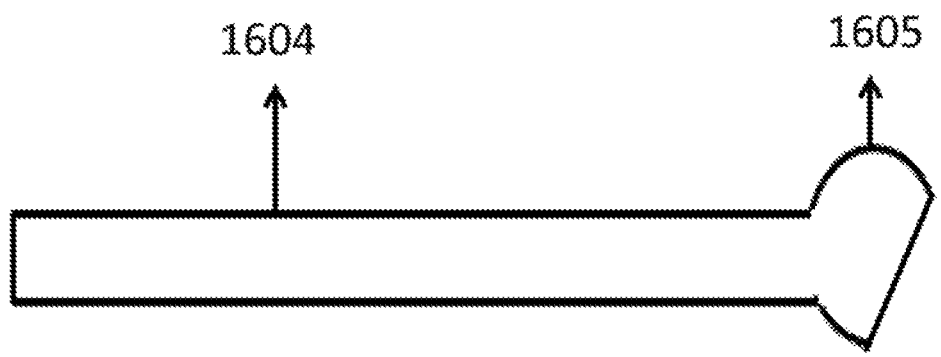

The wavelength of the imaging light, capture light, tissue altering light (e.g. UV eximer light), and ejection light can be different. In order to focus different light onto proper positions, it is important to consider the chromatic aberration from the focusing and relay optics in the optical configuration. For example, as shown in FIG. 16A, after the relay optics (1601), an achromatic focusing lens (1602) can focus light at different wavelengths to the boundary between the capturing material and the tissue. One exemplary design is a micro lens assembly. In the end, the reflective surface (1603) can deflect light beam to image the tissue at the side. Using an achromatic ball lens (1605) after relay optics (1604) is another solution (see FIG. 16B). The material of achromatic ball lens can have a small chromatic dispersion between the wavelength of capture, imaging and alteration light for focusing them to proper positions.

Figure 17:
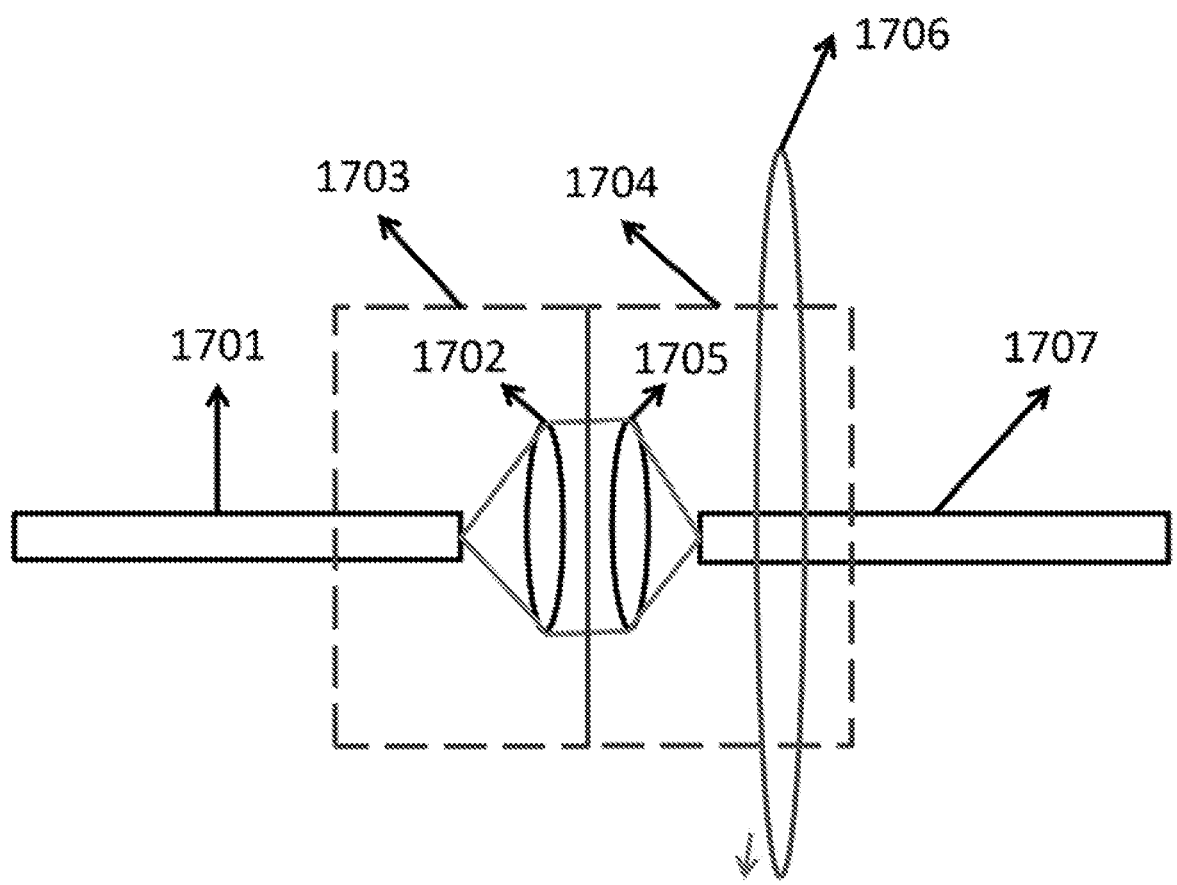
FIG. 17 is an illustration of an exemplary achromatic rotary junction.

In an exemplary embodiment, a rotary junction is used for coupling light from light source into a rotating optical fiber (see FIG. 17). At a fixed end (1703), a divergent light from fiber (1701) can be collimated by an achromatic collimation lens (1702). At the end (1704) that is rotating (1706), an achromatic focusing lens (1705) can focus the collimated beam into a fiber (1707). Achromatic optics (1702, 1705) are generally designed for maximizing the coupling efficiency of imaging, capturing and altering light at different wavelength.

Figure 18A:
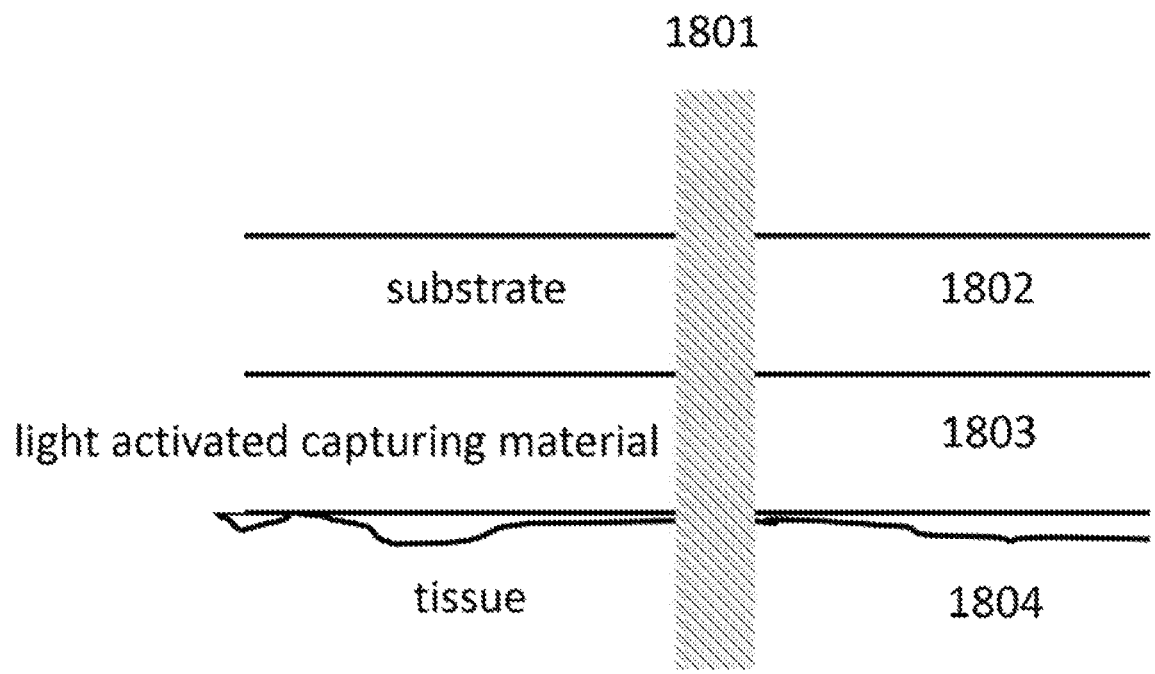
FIGS. 18A and 18B are illustrations of exemplary arrangements for coating layers on a substrate according to exemplary embodiments of the present disclosure.
Figure 18B:
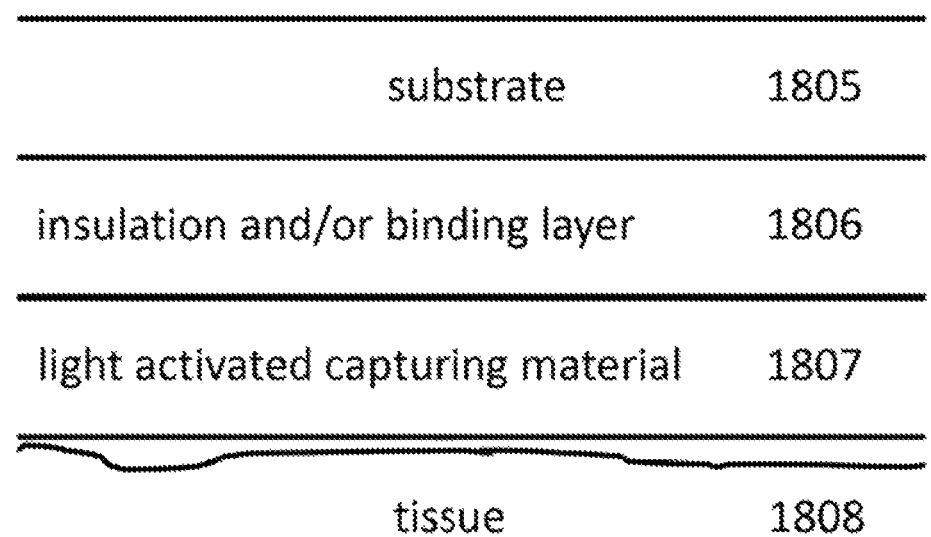

FIGS. 18A and 18B show the coating layers on an imaging device according to an exemplary embodiment of the present disclosure. For example, a light beam (1801) can penetrate through a substrate (1802) which is the housing of the device and reaches the light-activated capturing material (1803) and tissue (1804). The capturing material (1803) can have a strong binding force with the substrate (1802). After receiving light energy, the tissue/capturing material composite can be peeled off from the surrounding tissue without breaking the connection between the capturing material (1803) and the substrate (1802). If the capturing material (1807) may cause any damage to the substrate (1805) during the capturing process, for example, high temperature while the thermopolymer is melting, an insulation layer (1806) can be introduced between the capturing material (1807) and the substrate (1806). Moreover, if the target tissue (1808) has strong binding force with surrounding tissues, it can be challenging to peel off the target tissue without a strong connection between capturing material (1807) and substrate (1805). In this case, a binding layer (1806) that reinforces the connection can be used.

Figure 19:
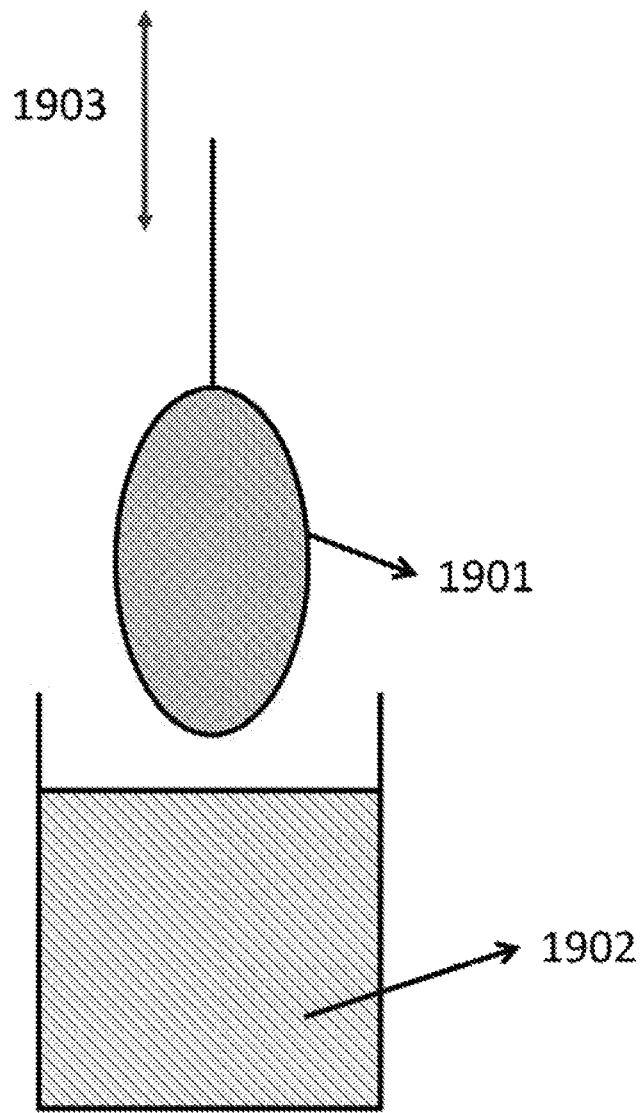
FIG. 19 is an illustration of an exemplary procedure for coating the device with dip coating according to exemplary embodiments of the present disclosure.
Figure 20:
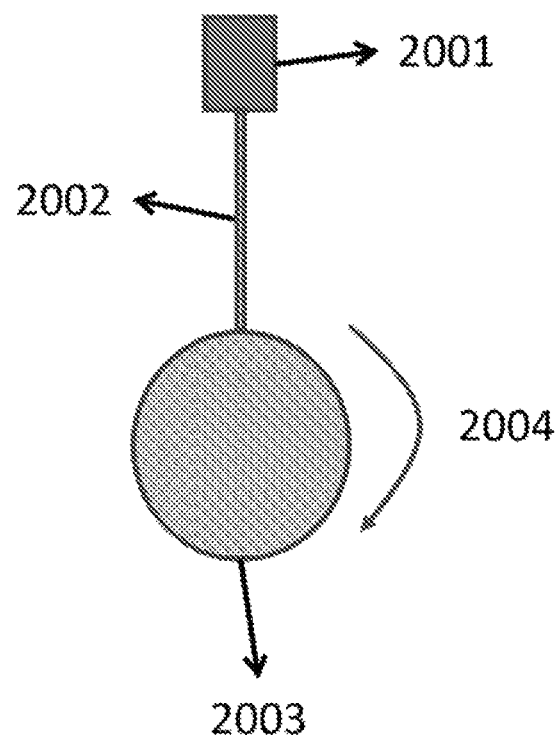
FIG. 20 is an illustration of an exemplary procedure for coating the device with dispense coating according to exemplary embodiments of the present disclosure.

FIG. 19 shows an exemplary coating procedure to coat the device with light-activated capturing material by dip-coating according to an exemplary embodiment of the present disclosure. For example, a device (1901) can be immersed in coating solution (1902) and can be gradually pulled out from the solution. The pulling speed (1903) controls the thickness of coating. FIG. 20 illustrates another way of coating with an exemplary coating procedure. For example, the dispenser (2001) can dispense the coating solution (2002) on the device (2003), which is mounted on a rotator. Depending on the rotation speed (2004), the thickness of coating can be adjusted.

Figure 21:
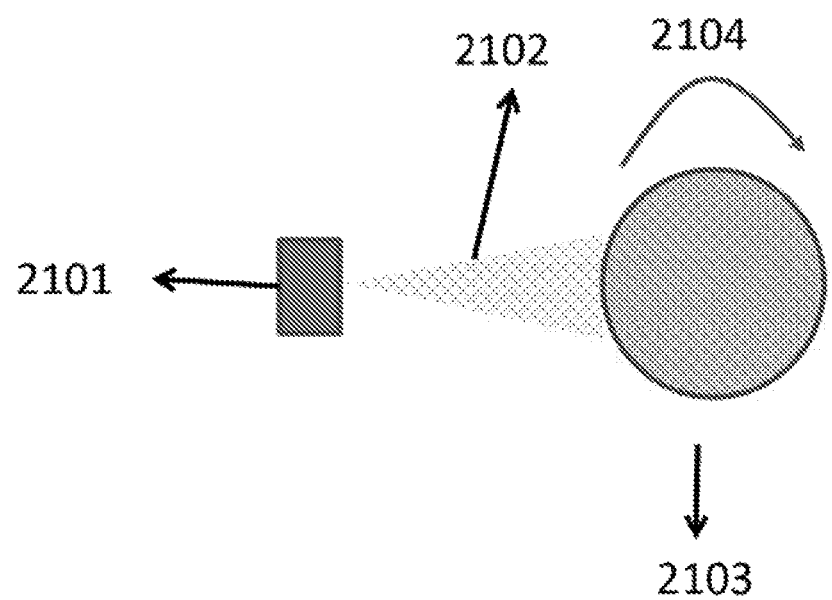
FIG. 21 is an illustration of an exemplary procedure for coating the device with spray coating according to exemplary embodiments of the present disclosure.
Figure 22:
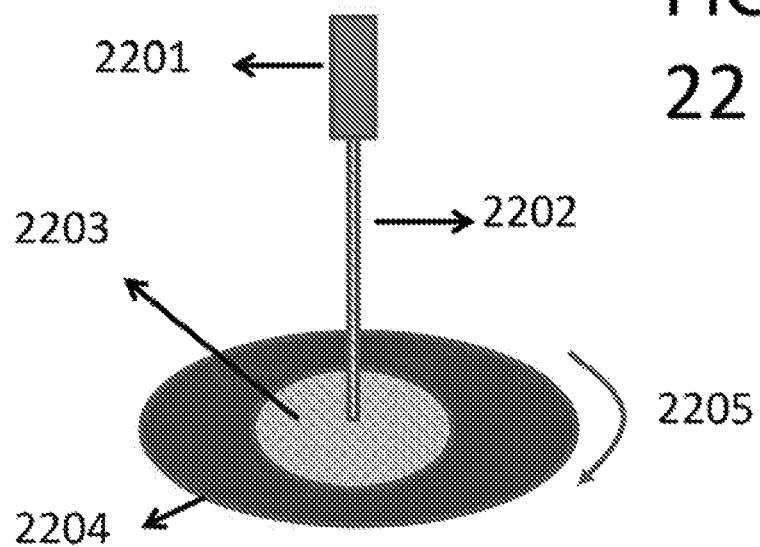
FIG. 22 is an illustration of an exemplary procedure for coating the device with spin coating according to exemplary embodiments of the present disclosure.

If accurate control of coating thickness is desirable, spray (see FIG. 21) or spin (see FIG. 22) coating are better options. From a spray dispenser (2101), a coating solution (2102) can be sprayed onto the device (2103). The device (2103) can be rotated in a uniform speed (2104). The speed of rotation (2104) and the dispense rate can determine the thickness of coating. Another exemplary way of accurate thickness control can be spin coating (see FIG. 22). For example, the dispenser (2201) can dispense the coating solution (2202) on the outer layer of the device, which can be fixed on a holder (2204). The rotation speed (2205) can determine the thickness of the coating.

Figure 23:
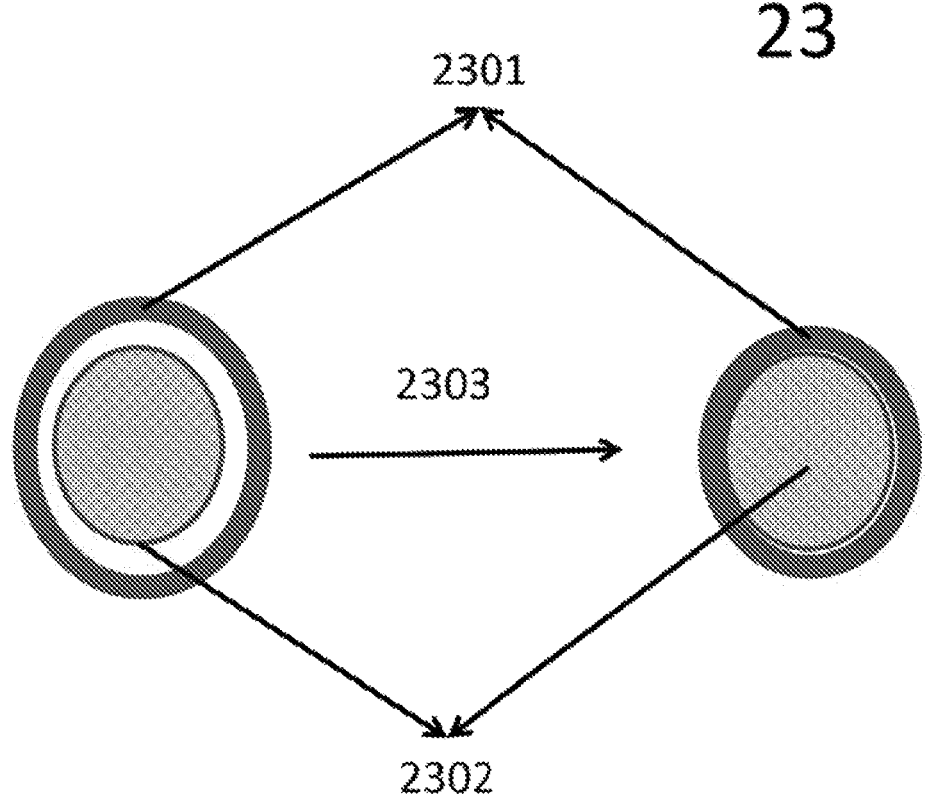
FIG. 23 is an illustration of an exemplary procedure for coating the device by melting the capturing material surrounding the device according to exemplary embodiments of the present disclosure.

It is also possible to coat the device by melting the material directly on the device (see FIG. 23). For example, a sheet of the capture material (2301) can be wrapped around the device (2302). Then, high temperature (2303) can be applied to melt the material. While melting, the material (2301) sticks to the device (2302) and after cooling down, the capture film (2301) becomes affixed to the device (2302).

Figure 24:
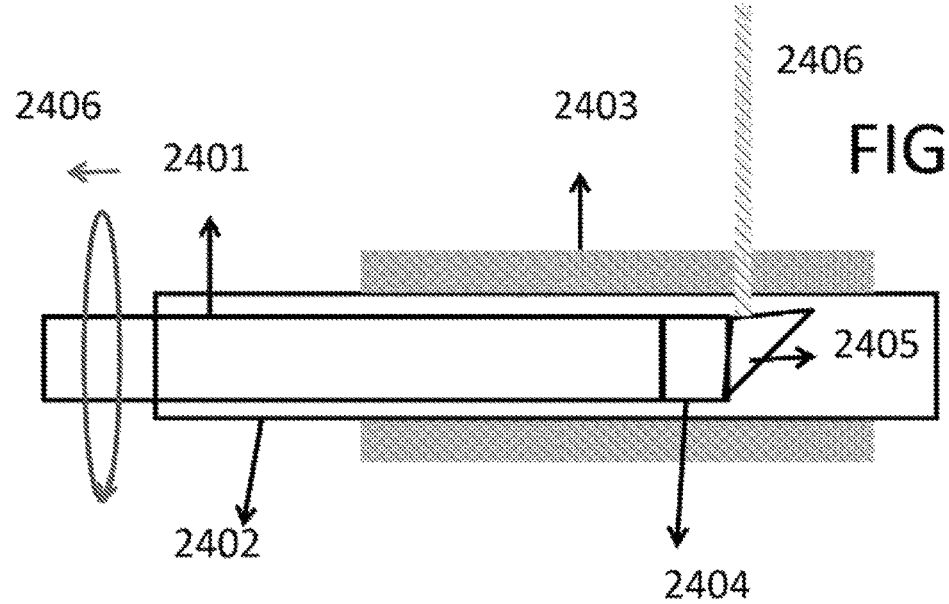
FIG. 24 is a cross-sectional view of an exemplary arrangement of a side-viewing device, according to an exemplary embodiment of the present disclosure, for the purpose of imaging and tissue capturing.

It is possible to coat other imaging devices with the light activated capturing material, which facilitates the imaging device to capture tissues. For example, FIG. 24 illustrates the coating on a side-viewing imaging device. One or more of exemplary components of a side-viewing device can include relay optics (2401), focusing optics (2404) and/or a reflective surface (2405). Relay optics (2401) can deliver and collect light to and from the tissue. Such relay optics (2401) can include, but is not limited to, optical fiber, fiber bundle, GRIN rod lens, and free space optics, etc. Focusing optics (2404), which focus light beam, can include, but is not limited to, lens, GRIN lens, ball lens, etc. Reflective surface (2405) can deflect light to image the tissue on the side. Delicate optics can be protected by a transparent sheath or window (2402), which is also the substrate to the capture coating (2403). The capture film can be therefore affixed to the transparent sheath housing (2402).

While the light beam can be scanning (2406) and surveying the tissue, at least one of the capture light, tissue altering light, and imaging light is delivered through the same optics. The capture electromagnetic radiation can activate the coating (2403) on a specific region to capture the selected tissue. An alternate exemplary embodiment of this device can include a needle based device as the housing (2402) where the needle is at least partially transparent and is coated by or associated with an external capture film. Imaging can occur through the partially transparent needle and regions of interest are identified in the microscopic image. Then, tissue alteration and capture light can be transmitted through the needle (2402) and film (2403). This electromagnetic radiation alters a characteristic of the film (2403), such as its temperature, which causes a material change in the film such as melting, where the film becomes intercalated with the target tissue and then upon curing of the film or otherwise cooling of the film, the physical characteristics of the film change, such as hardness, and the tissue becomes incorporated into the film. The tissue can be removed from the body when the housing or needle is removed from the body and the tissue is then disassociated from the device for subsequent RNA, DNA, protein characterization, or other advanced cellular or molecular analysis.

Figure 25:
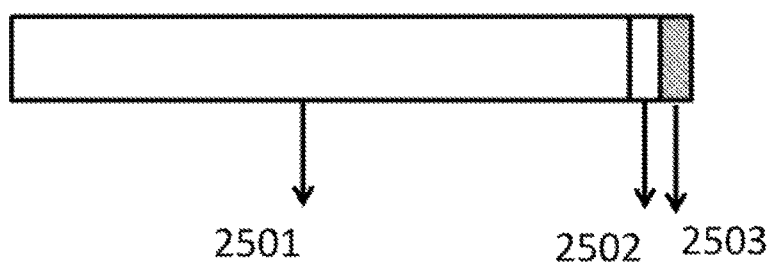
FIG. 25 is a cross-sectional view of an exemplary arrangement of a forward-viewing device, according to an exemplary embodiment of the present disclosure, for the purpose of imaging and tissue capturing.

In yet another exemplary embodiment, the capture coating (2503) can be coated on a forward-imaging device (as shown in FIG. 25). Exemplary components of a forward-imaging device can include one or more of a relay optics (2501) and focusing optics (2502). Relay optics (2501) can deliver and collect light to and from the tissue. It includes, but is not limited to, optical fiber, fiber bundle, GRIN rod lens, and free space optics, etc. Focusing optics (2502), which focus light beam, can include, but is not limited to, lens, GRIN lens, ball lens, etc. The capture material (2503) in the front of the device contacts the tissue in front. If suspected tissue is identified, capture light can activate the coating (2503) in the front to capture the selected tissue.

Figure 26:
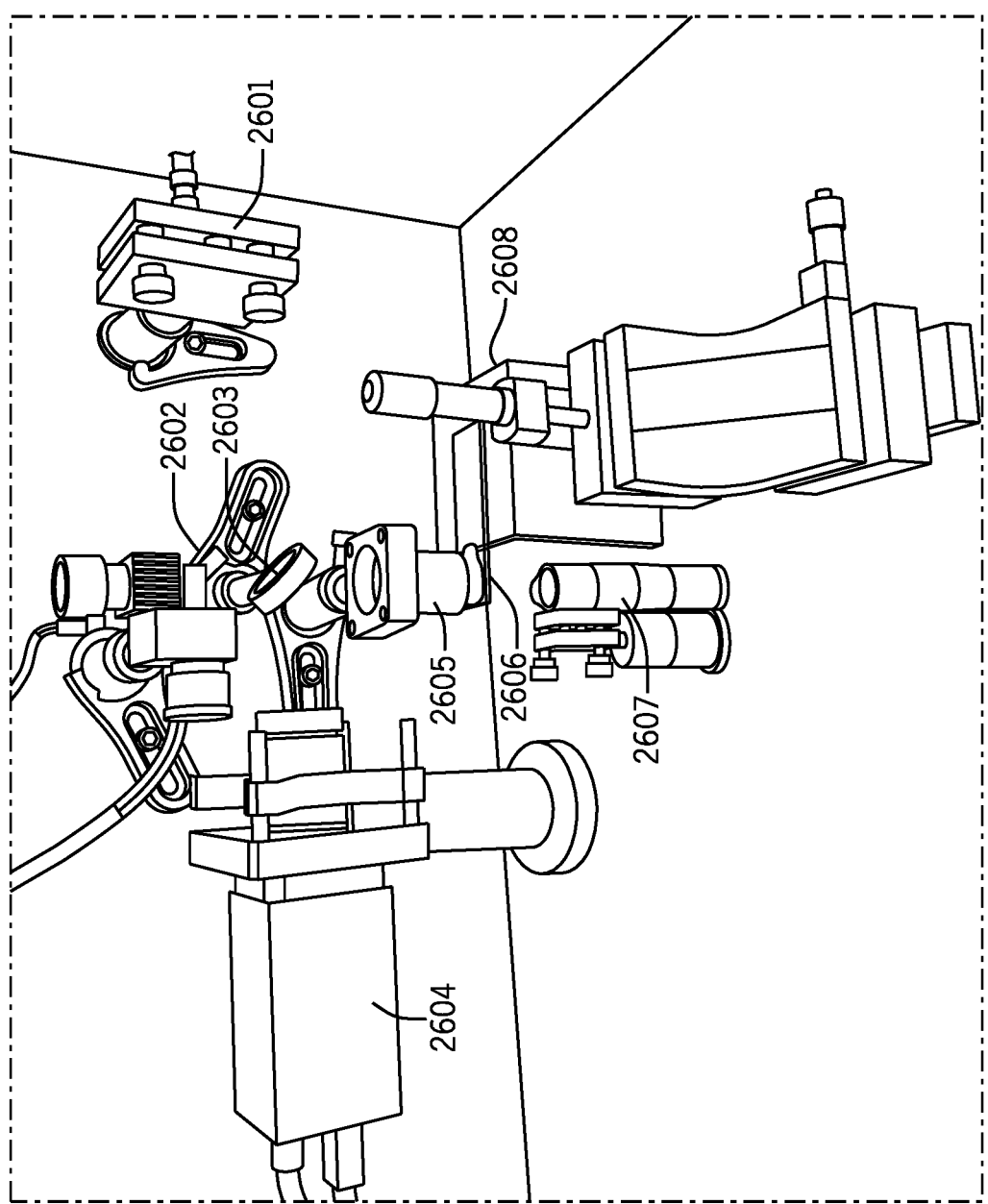
FIG. 26 is a photograph of the system according to a yet further exemplary embodiment of the present disclosure.

FIG. 26 shows a photograph of a system that is capable of capturing cells from hydrated ex vivo bulk tissue. For example, capture light injects into the system through an optical fiber (2601). A pair of galvo mirrors (2602) controls the position of the light spot.

After passing through a long pass filter (2603), an objective lens (2605) focus the light beam on a capturing membrane and tissue (2606). A translational stage (2608) positions the sample into the field of view. The back reflected light from the sample are deflected into a camera (2604), which can confirm whether the tissue and membrane is placed in the focus. After capture light illumination, the capture membrane can be peeled off from the tissue and placed on a glass slide. Illumination from the bottom (2607) provides bright-field microscopic image.

Figure 27:
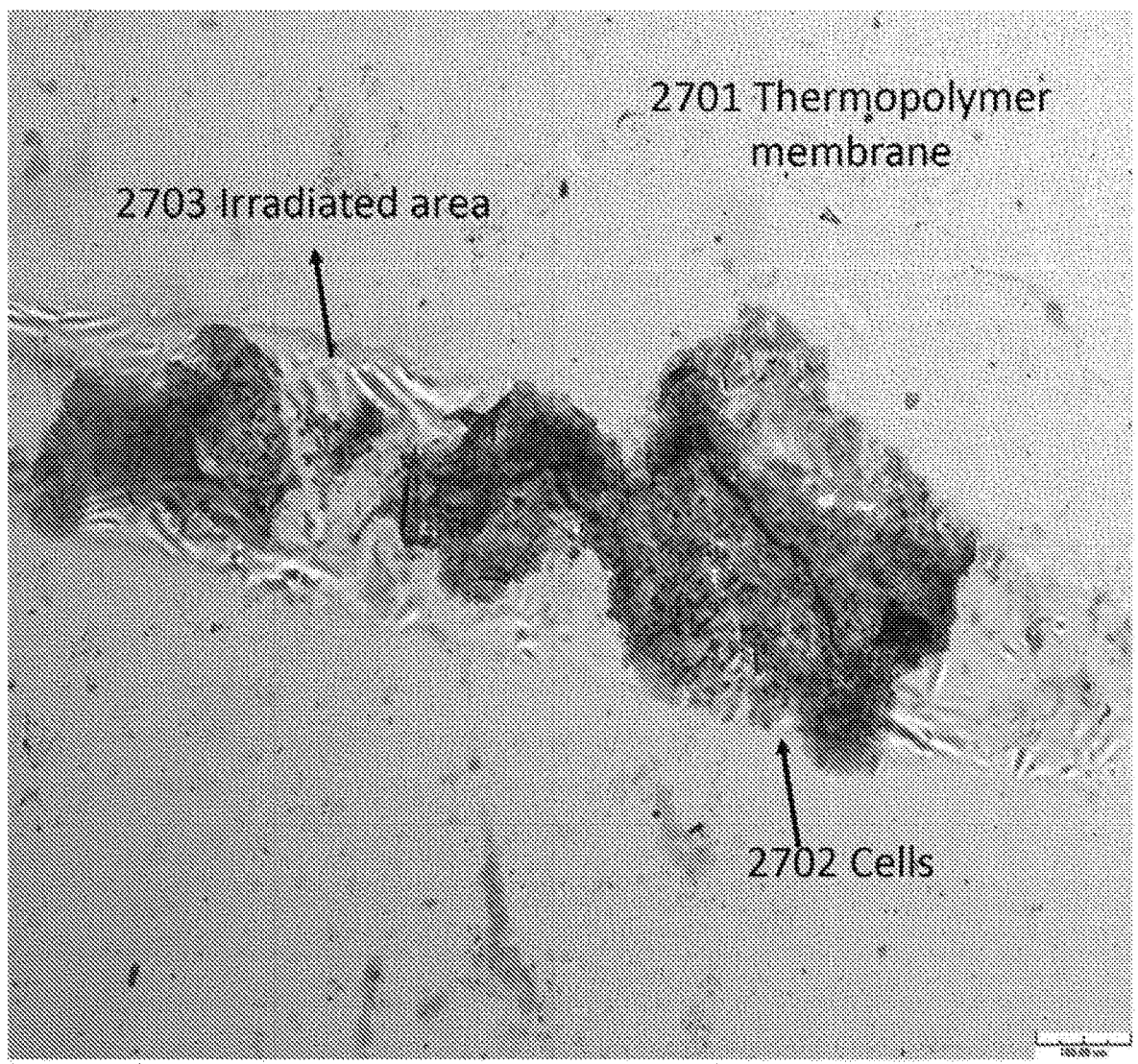
FIG. 27 is an illustration of exemplary microscope image data obtained from the tissue captured on the capturing film from the exemplary system shown in FIG. 26.

FIG. 27 shows an exemplary result of using a thermopolymer membrane (2701) to capture columnar cells (2702) from an ex vivo small intestine. For example, the polymer irradiated by capture light (2703) successfully capture large amount of cells (2702, stained with hematoxylin) under aqueous condition. This exemplary data demonstrates the feasibility of using light-activated capture material to capture cells from bulk hydrated tissue.

Figure 28A:
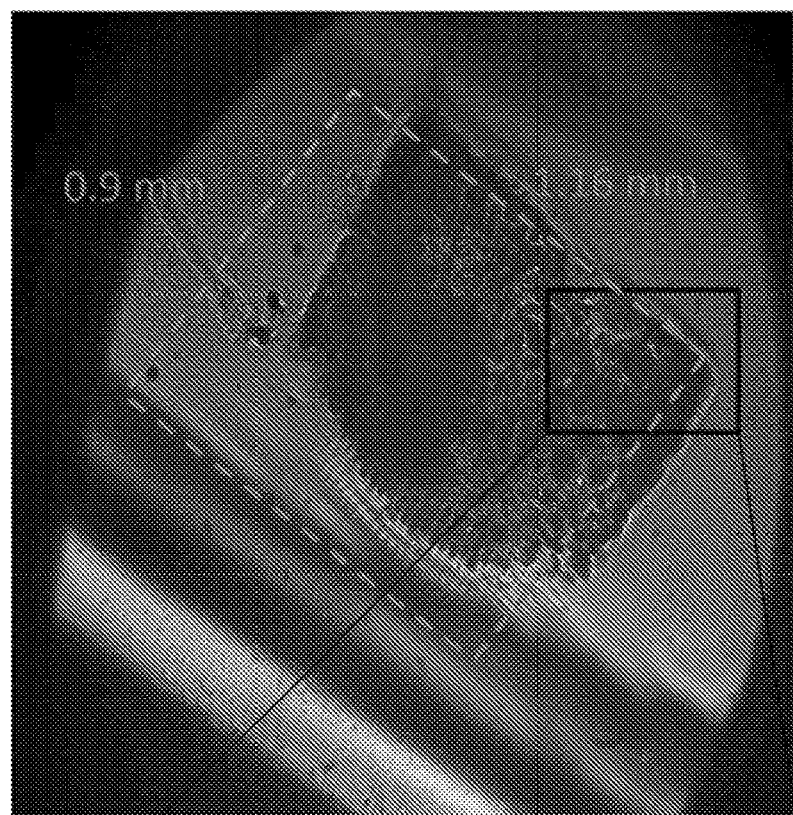
FIGS. 28A and 28B are illustrations of exemplary microscope image data obtained from the tissue captured on the capturing film from the exemplary system of FIG. 20.
Figure 28B:
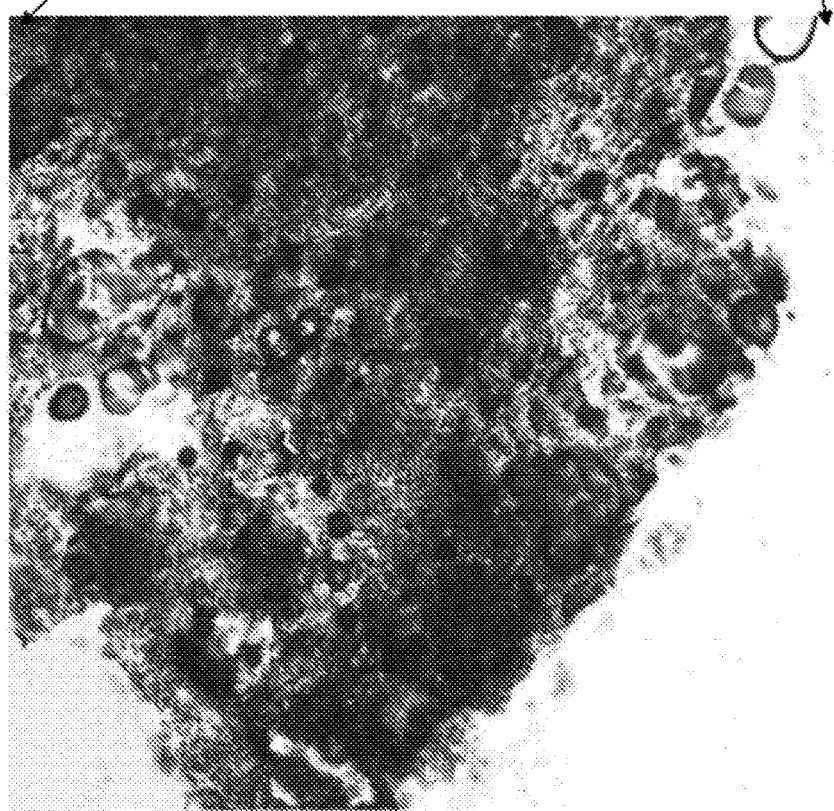

FIGS. 28A and 28B show a bright field image of the capture membrane and the captured tissue. The dark area within the red rectangle is the captured tissue. Black rectangle indicates the zoom-in image that is shown in FIG. 28B. From the Hematoxylin stained tissue (FIG. 28B), the nuclei with a dark blue color can be easily identified, which indicates that the integrity of cell nucleus was not disrupted by the capturing procedure.

Figure 29:
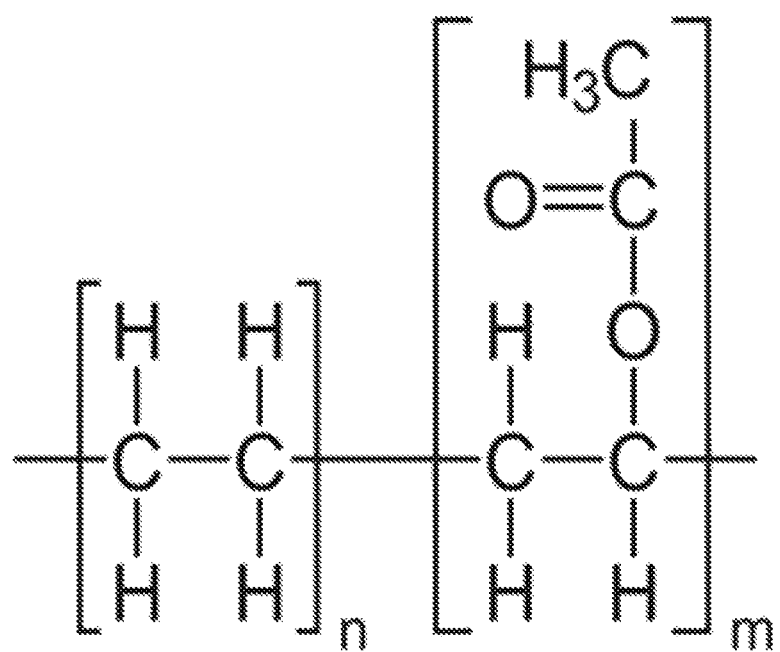
FIG. 29 is an illustration of an chemical structure of an exemplary thermopolymer, ethylene-vinyl acetate (EVA), which can be used as the matrix of light-activated capturing material.

FIG. 29 shows the chemical structure of a potential candidate of the matrix of light-activated capturing material, ethylene-vinyl acetate (EVA). EVA is a copolymer of ethylene and vinyl acetate. As the percent of Vinyl acetate increase, the freezing and melting points of EVA decrease. In order to melt EVA without generating excessive thermo-damage to the cells, EVA with low melting point (60-70° C.) is typically used (Dupont Elvax 200W, 410, 205W and 4310). Special photothermal agent is mixed with the polymer to convert photon energy to thermal energy. Photothermal agent with large light absorption cross section enables highly localized melting at the illumination spot. Subcellular resolution can be achieved with high NA optics. Depending on the property of photothermal agents, different approached can be used for mixing the agent with EVA.

FIG. 30A depicts the flow diagram of mixing EVA with organic-soluble agent according to an exemplary embodiment of the present disclosure. After EVA being dissolved in organic solvent (step 3001), the agent is added to the solution (step 3002). The impurity or aggregated agent in the solution is removed by centrifuge (step 3003). In order to coat the polymer onto a device, proper viscosity is required. A solution with high viscosity can be obtained by evaporating the solvent (step 3004). With proper viscosity, the solution can be coated around the device using the exemplary procedures illustrated in FIG. 19-23 (step 3005). After solvent evaporation, a solid EVA film with photothermal agent is coated around the device (step 3006). On the other hand, it is also possible to mix EVA with water-soluble agents. However, in this case, chemical mixture by dissolving both EVA and agent in the same solvent is not possible. After EVA dissolve in organic solvent (step 3007), as shown in FIG. 30B, the solution can be adjusted to a proper viscosity for mechanical mixture (step 3008). High viscosity is necessary for mechanical mixture. The water solution of the photothermal agent can be mixed with the EVA solution by strong mechanical stirring force, such as ultrasonic mixing device (step 3009). After mixture, the polymer can be coated around the deice (step 3010), then the entire device can be placed in a vacuum chamber for removing the residue solvent and degassing (3011).

Figure 33A:
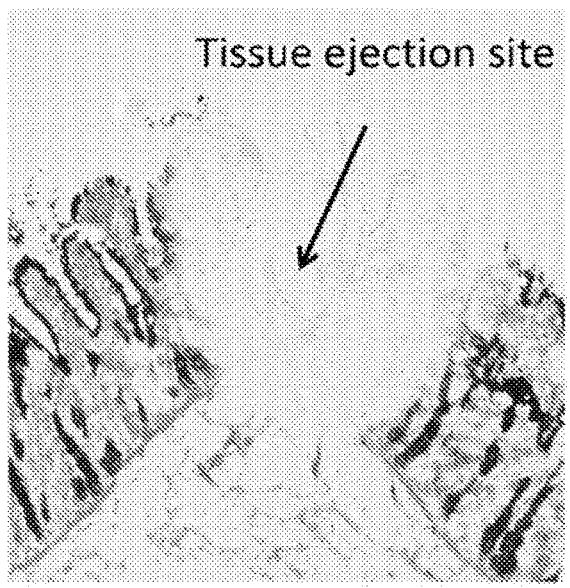
FIG. 33A is an illustration of exemplary cross-sectional histology image data obtained from the tissue being illuminated by the tissue alteration light.
Figure 33B:
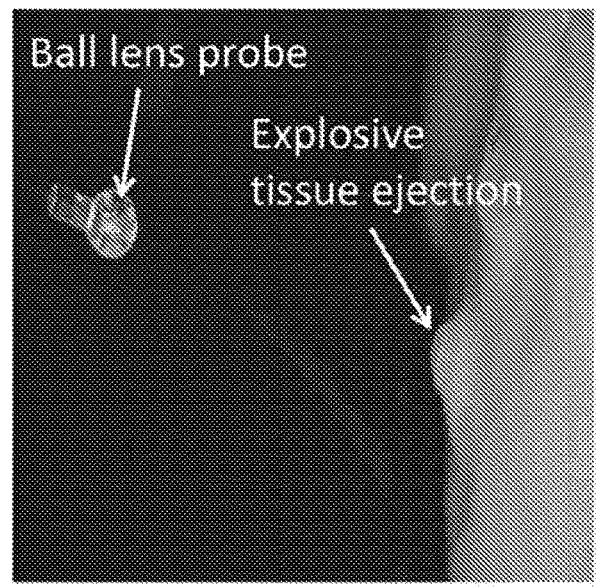
FIG. 33B is a photograph of exemplary explosive tissue ejection induced by the tissue alteration light.
Figure 33C:
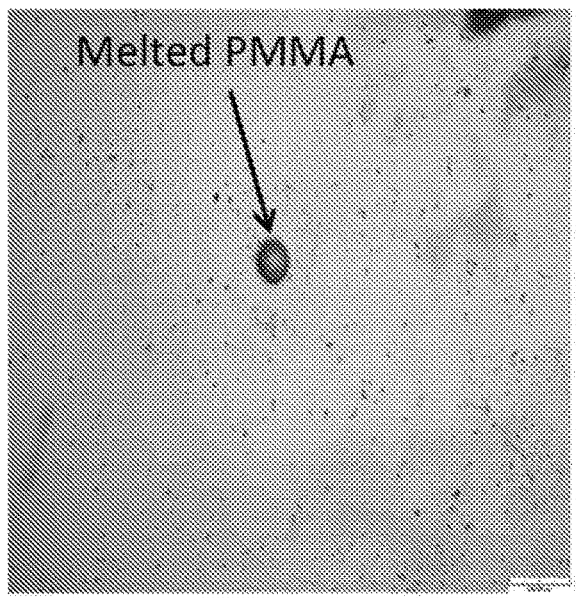
FIG. 33C is an illustration of exemplary microscopic image data of melted capture material induced by the tissue alteration light.
Figure 33D:
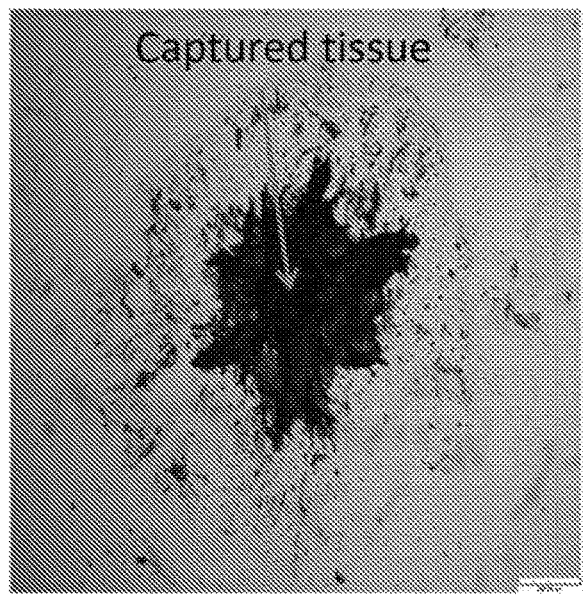
FIG. 33D is an illustration of exemplary microscopic image data of captured tissue on capture material, with the captured tissue being ejected by tissue alteration light.
Figure 34:
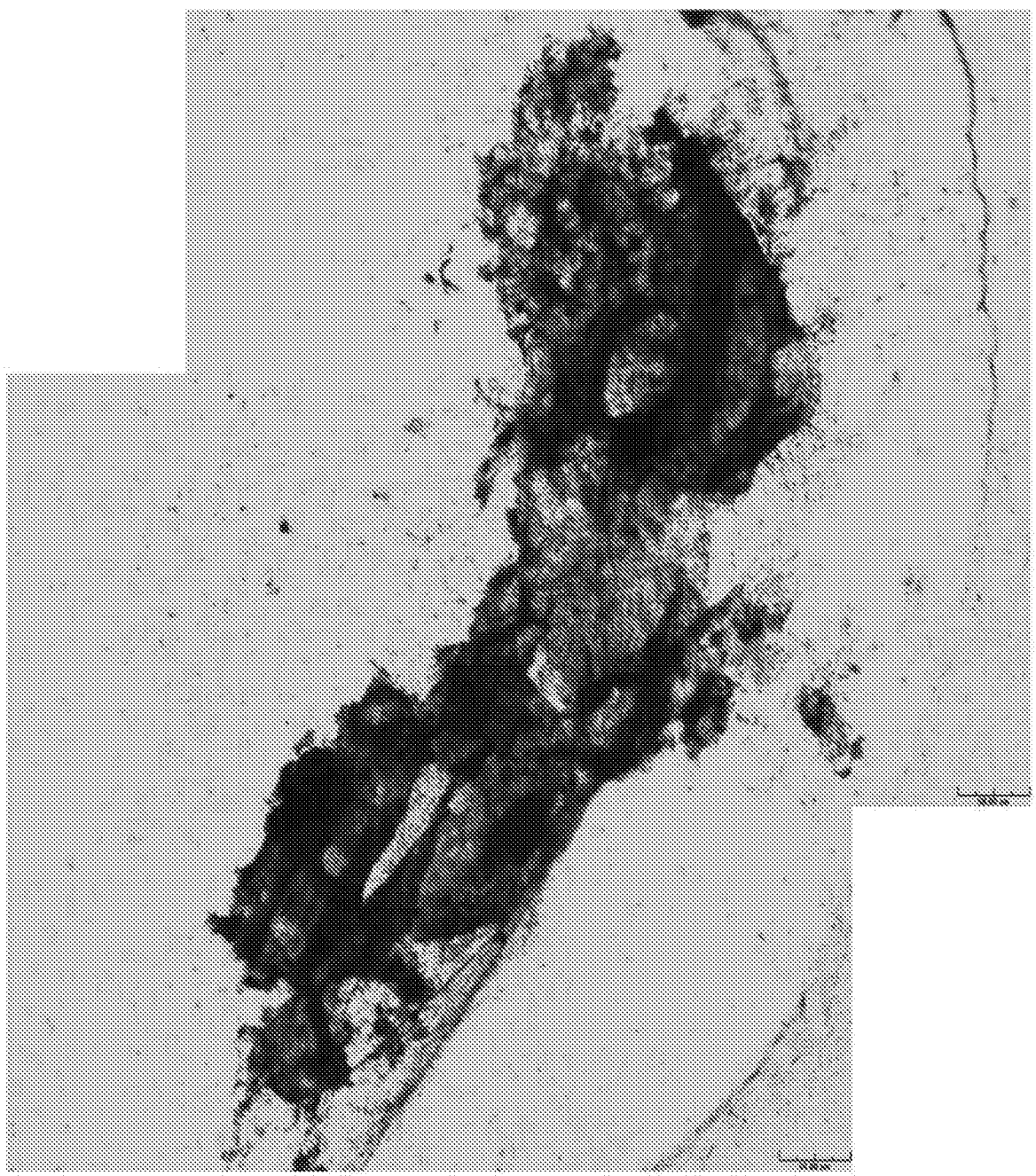
FIG. 34 is an illustration of exemplary microscopic image data of captured tissue on capture material with the captured being is ejected by tissue alteration light and is captured at 0.8 mm away from the bulk tissue.

In yet another exemplary embodiment, a new paradigm of tissue capturing is developed. Instead of melting the capturing material and integrating it with adjacent tissue, it is possible to eject the tissue from the bulk tissue with laser ablation (see FIG. 33A) and then capture the hot ejected tissue with capture material (FIG. 33D). The laser energy is absorbed and converted to heat by the endogenous water in tissue. The heated water becomes steam, which is confined within tissue matrix until the pressure overcomes the holding force. FIG. 33B shows the bulging surface caused by the accumulating steam within tissue matrix of esophagus. FIG. 33C shows that the capture material (PMMA) is melted by the hot water steam. When the steam pressure is larger than the holding force from tissue matrix, tissue (FIG. 33D) is ejected and fused with the melted capture material. FIG. 34 shows an ejected tissue, which is captured at 0.8 mm away from tissue surface by polymethyl methacrylate (PMMA). The tissue is stained with hematoxylin for visualization.

Figures 31A, 31B, 31C:
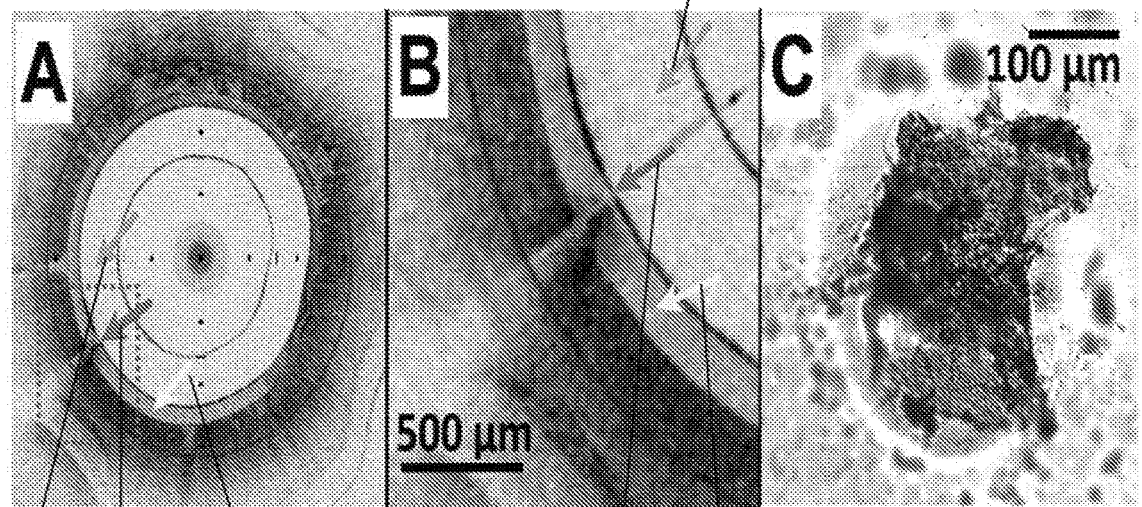
FIGS. 31A and 31B are illustrations of exemplary optical coherence tomography (OCT) image data obtained from the tissue captured on the EVA film coated on a TCE device.
FIG. 31C is an illustration of exemplary microscopic image data obtained from the tissue captured on the EVA film.
Figure 32:
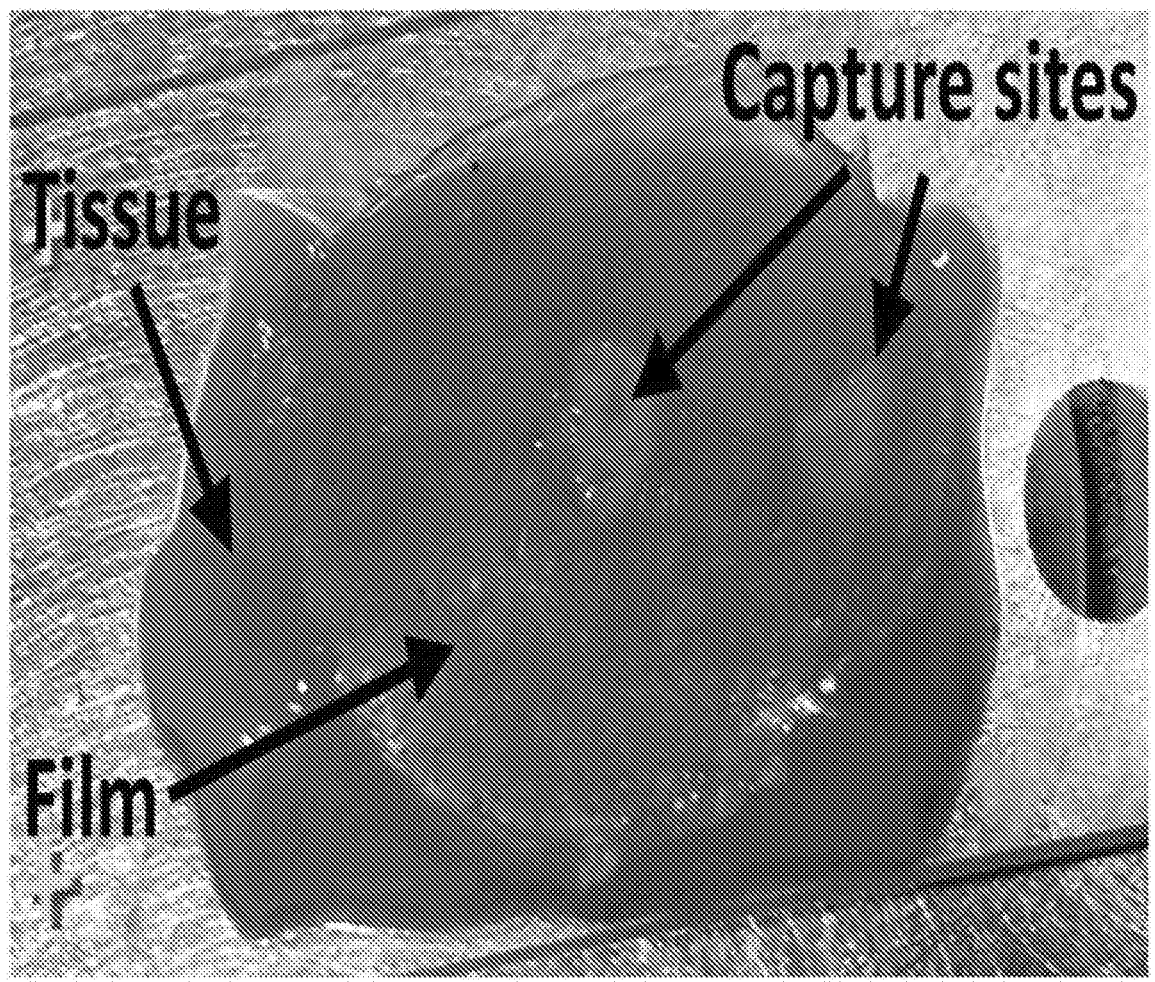
FIG. 32 is an illustration of exemplary microscopic image data obtained from the tissue being illuminated by a tissue alteration light.

Another benefit of using laser ablation for capturing is that it may leave a visible mark on the host tissue (see FIG. 32), which enables the follow-up or correlation studies. FIG. 31A shows an in-house-fabricated 300 μm-thick EVA polymer film was affixed around an existing OCT TCE device. The LCM-enabled capsule was placed atop fresh, full-thickness swine intestine. The polymer (see FIGS. 31A and 31B—arrow 3103) can be clearly seen in the OCT TCE image, in between the capsule wall (see FIGS. 31A and 31B—arrow 3101) and the tissue. Capture light (650 mW, 1450 nm) was transmitted through the capsule's imaging optics to the tissue. A single 35-μm diameter spot was irradiated. Following capture laser exposure for 30 seconds, the OCT images of the film and tissue were visibly altered (see FIGS. 31A and 31B—arrow 3102), features that may be used to verify successful tissue sampling. Tissue was captured onto the capsule over an area that was ~100 times greater than that of the spot itself (see FIG. 31C).

Figure 35A:
FIG. 35A is an illustration of exemplary microscopic image data of captured tissue on capture material, with the captured tissue binding to the capture material through photothermal cross-links.
Figure 35B:
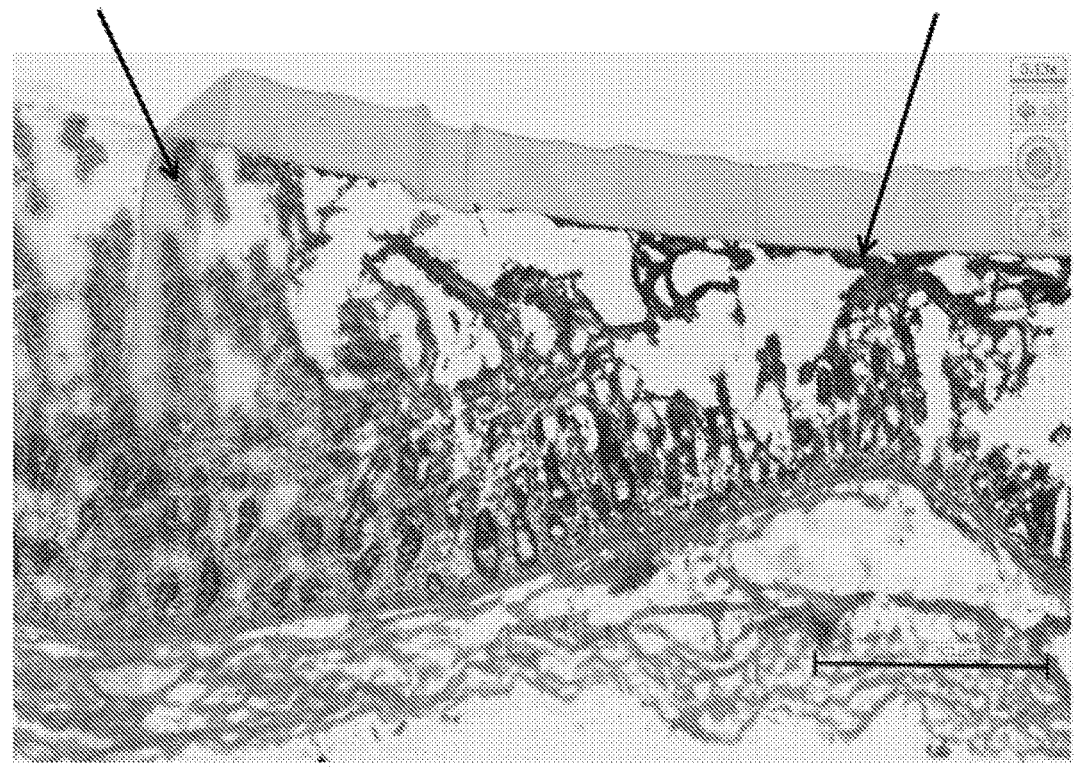
FIG. 35B is an illustration of exemplary cross-sectional histology image data obtained from the tissue being illuminated by tissue alteration light with capture material on top.

The capture efficiency can be significantly improved by utilizing photothermal cross-link. Certain chemical cross-links between functional groups are encouraged in heated water. For example, the hydroxyl group on the capture material can form an ester bond with the carboxylic acid in tissue in heated aqueous environment. FIG. 35A shows the tissue is captured on a silicone hydrogel, which has abundant hydroxyl group. FIG. 35B shows that the dehydrated tissue at the illuminated area is firmly attached to the surface and no tissue attachment at non-illuminated area. The photothermal energy at the illuminated site triggers the cross-linking reaction which allows the silicone hydrogel to capture tissues within its adjacent area.

Figure 36A:
FIG. 36A is an illustration of exemplary microscopic image data of captured tissue on capture material, with the capture tissue being ejected by a pulse laser.
Figure 36B:
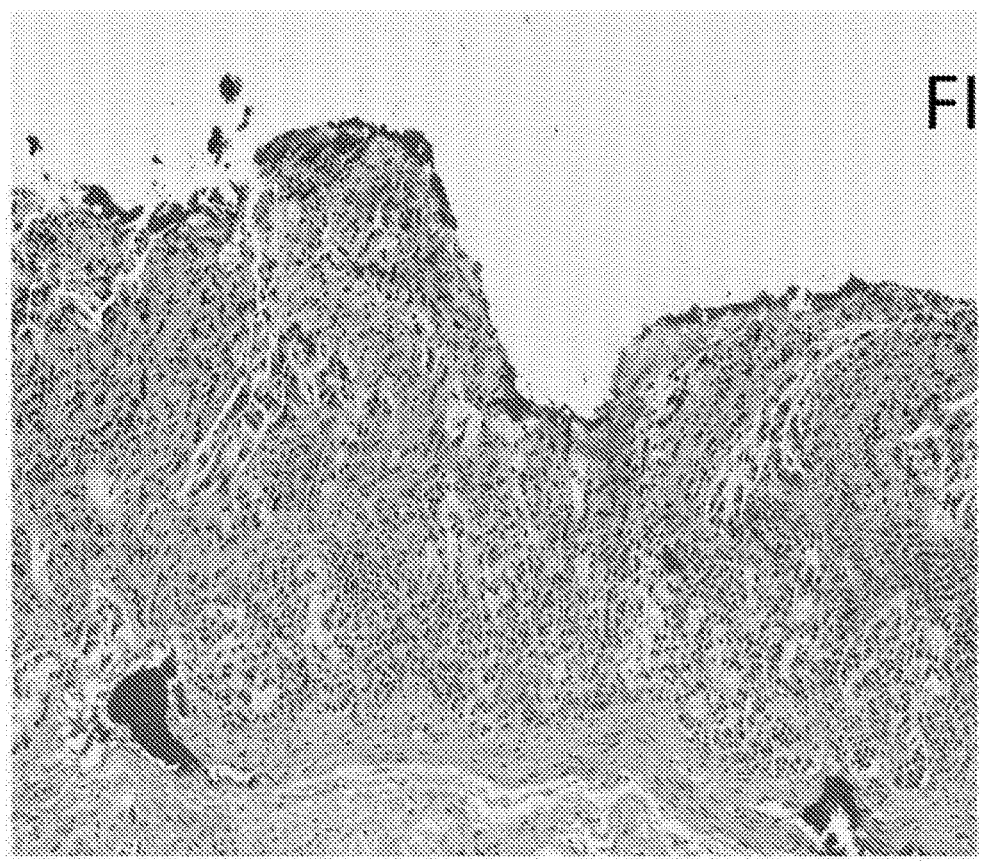
FIG. 36B is an illustration of exemplary cross-sectional histology image data obtained from the tissue being illuminated by a pulsed tissue alteration light.

Depositing energy in a confined temporal scale, which is much shorter than the heat diffusion scale, can greatly reduce the dissipation loss and thus heat the tissue and capture material much more efficiently. If capturing time is much shorter than imaging time per frame, it is possible to monitor capturing with real time imaging. If pulsed light is used, it can be transmitted through the same single mode fiber utilized for imaging or, if multi-mode, through the inner cladding of a double-clad fiber (DCF). FIG. 36A shows the captured tissue ejects by a nanosecond laser. FIG. 10B shows ejection site with minimal residual thermal damage in the surround tissues. The figure demonstrates short pulse laser can efficiently eject tissue with minimal collateral thermal damage.

Figure 37:
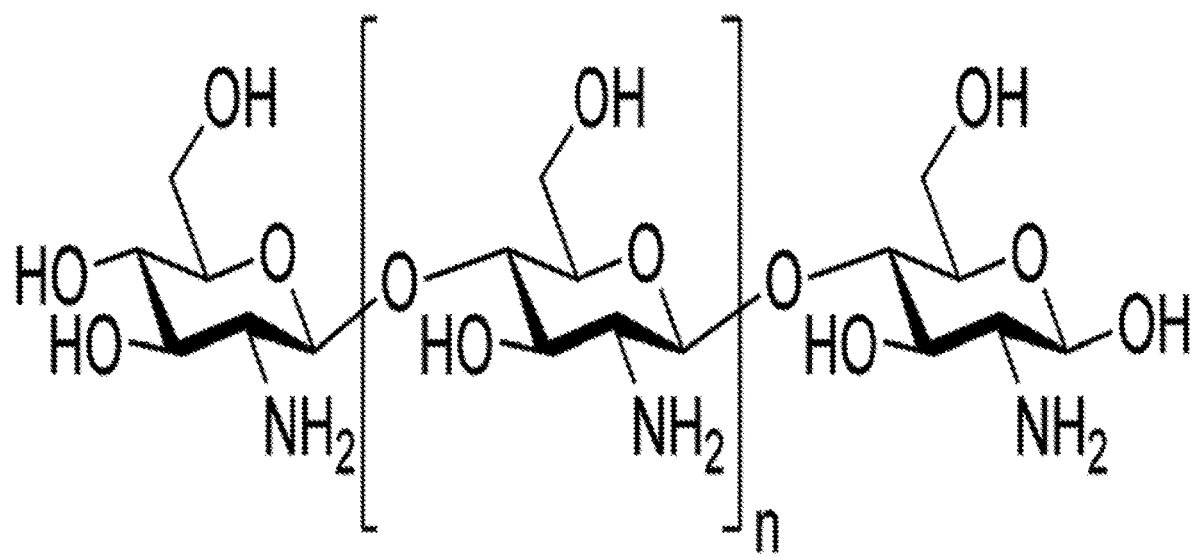
FIG. 37 is an illustration of an exemplary chemical structure of chitosan, which is a naturally occurring linear polysaccharide that can bind tissue upon dehydration or any other chemical substance that can attach to tissue or cells and affix these tissue or cells to the substance which is operatively attached to the housing of the device.
Figure 38:
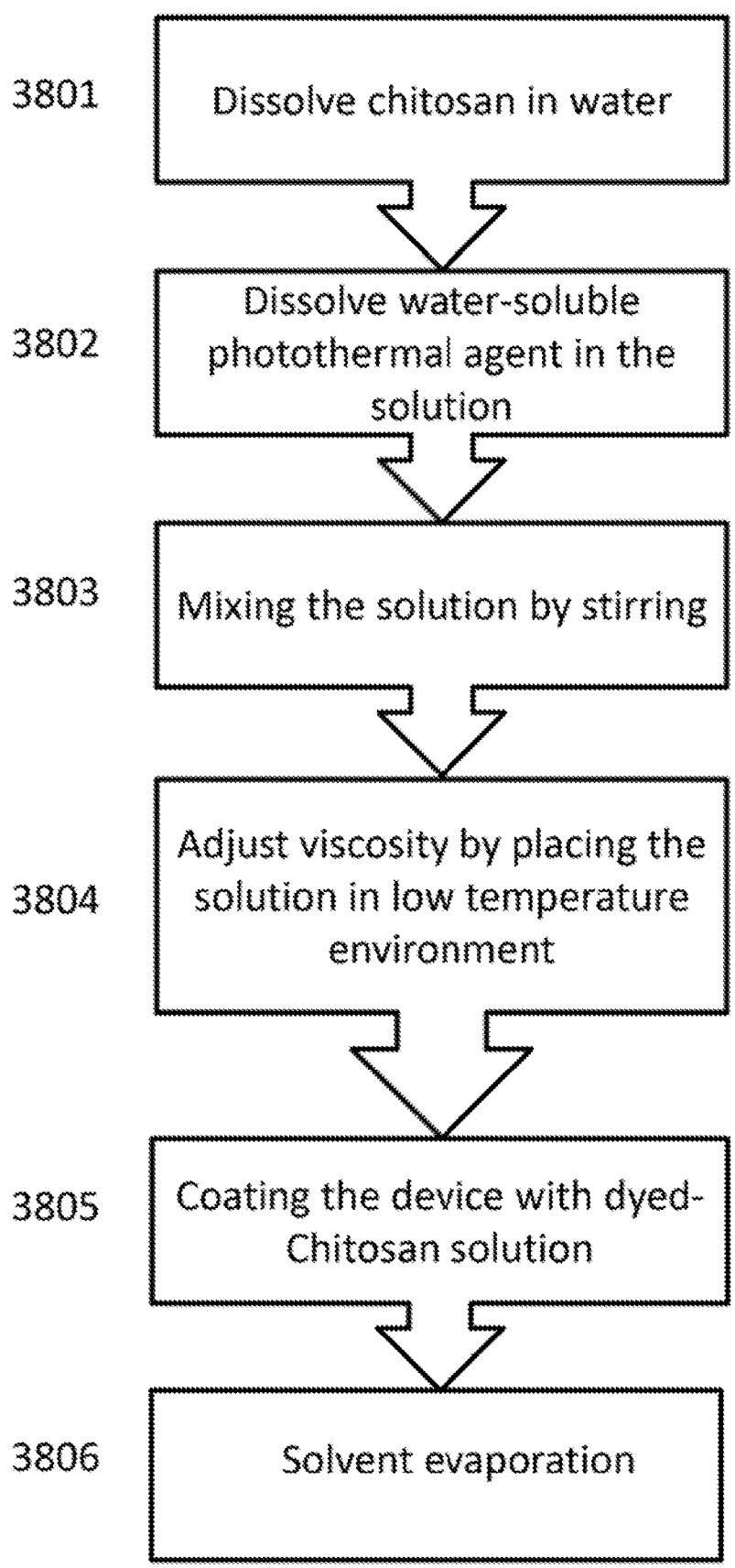
FIG. 38 shows a flow diagram of an exemplary procedure for mixing chitosan with water-soluble photothermal agents according to an exemplary embodiment of the present disclosure.

Besides EVA, it is also possible to use chitosan as the capture material. The chemical structure is shown in FIG. 37. Chitosan is a polysaccharide, which has good biocompatibility and has been used for tissue repair, drug delivery, tissue engineering and blood clotting. It is also possible to mix chitosan with photothermal agents, which can melt chitosan for tissue capturing. As shown in the exemplary procedure of FIG. 38, chitosan can be dissolved in water (step 3801) with water-soluble photothermal agents (step 3802). After mixing (step 3803), the solution is placed in low temperature (4° C.) environment to increase its viscosity (step 3804) for coating. Then, the gelatinous solution is casted on the substrate or coated around the device (step 3805). It may take two weeks to evaporate the solvent (water) and obtain a solid water-insoluble film (step 3806).

Figure 39:
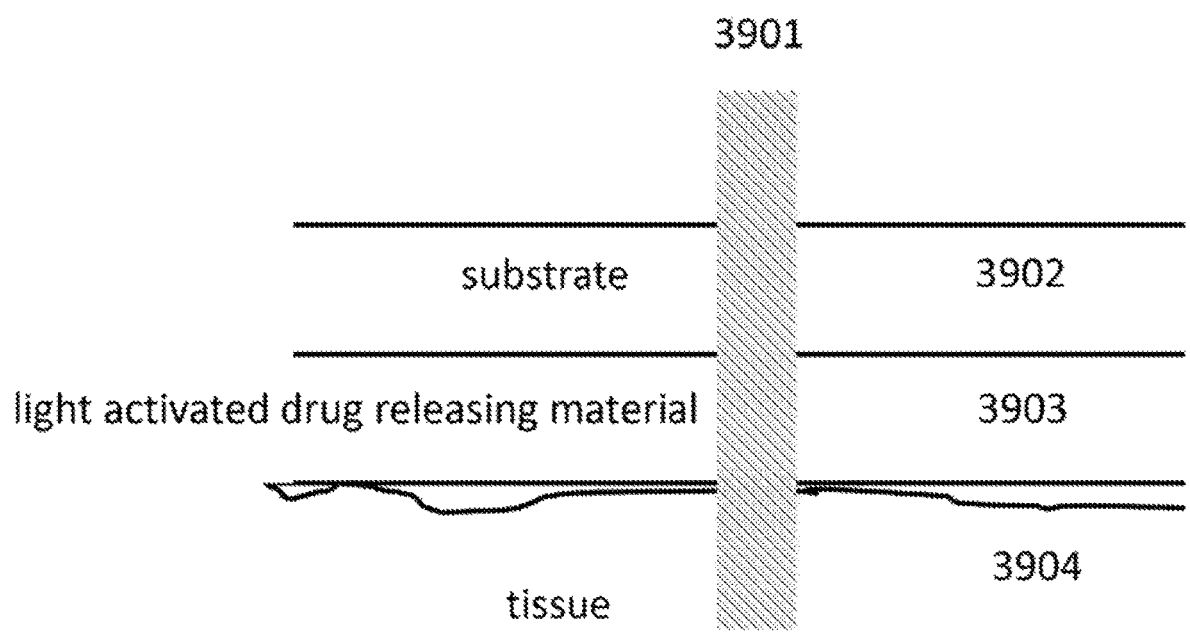
FIG. 39 is an illustration of exemplary arrangements of light activated drug releasing coating layer on a substrate, according to exemplary embodiments of the present disclosure.

It is also possible to change the light activated capturing material to drug releasing material for high precision treatment. FIG. 39 shows that the drug containing material (3903) can be coated around the outer surface of an imaging device (3902). Once a diseased area (3904) is identified in field of view, a releasing light (3901) is delivered to the selected area. The releasing light (3901) can trigger a photochemical reaction or structural change or generates hot water steam that releases the drug to the illuminated area.

Figure 40:
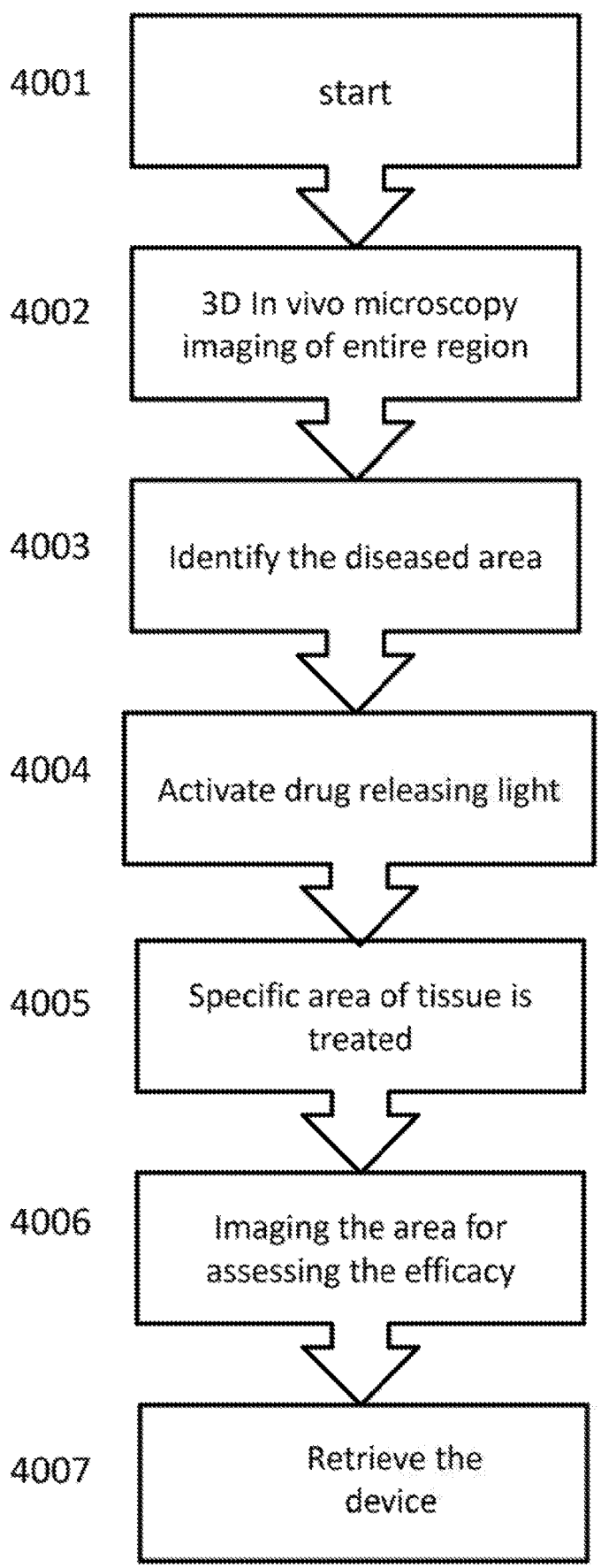
FIG. 40 is a flow diagram of an exemplary procedure for a light activated drug delivery with real-time imaging according to an exemplary embodiment of the present disclosure.

FIG. 40 shows a flow diagram of imaging guided microtreatment procedure according to an exemplary embodiment of the present disclosure. For example, in the beginning (step 4001), the imaging device is placed to the region of interest. Then, 2D/3D in vivo microscopy can be performed to survey the region of interest (step 4002). After the diseased area is identified (step 4003), drug releasing light can be activated (step 4004). Drug releasing light release drug to treat a specific area of tissue (step 4005). After treatment, another imaging can be performed with the same device for assessing the efficacy of the treatment (step 4006). In the end (step 4007), the device is retrieved from the patient.

The foregoing merely illustrates the principles of the present disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system, SECM system, OBM system or other imaging systems capable of imaging in vivo or fresh tissues, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, U.S. Patent Publication No. 2002/0122246, published on May 9, 2002, U.S. Patent Application 61/649,546, U.S. patent application Ser. No. 11/625,135, and U.S. Patent Application 61/589,083, the disclosures of which are incorporated by reference herein in their entireties. It will thus be appreciated that those skilled in the art will be able to devise numerous systems, arrangements and methods which, although not explicitly shown or described herein, embody the principles of the present disclosure and are thus within the spirit and scope of the present disclosure. Further, various exemplary embodiments described herein can be interchangeably used with all other exemplary described embodiments, as should be understood by those having ordinary skill in the art. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A capturing system for imaging and capturing a sample from a tissue, comprising:
    a capture membrane associated with the tissue;
    an optical system optically coupled to the capture membrane and the tissue; and
    a capture source which is configured to emit a spot of light radiation via the optical system onto the capture membrane to cause a portion of the tissue to attach to the capture membrane to produce the sample.

2. The system of claim 1, wherein the optical system comprises an imaging system,
    wherein the imaging system is configured to obtain images of the tissue.

3. The system of claim 2, wherein the spot of illumination from the capture source is configured to be scanned over the tissue to cause the portion of the tissue to attach to the capture membrane to produce the sample.

4. The system of claim 3, wherein the spot of illumination from the capture source is configured to be scanned over the tissue using a galvanometer mirror.

5. The system of claim 3, further comprising a translational stage coupled to the tissue,
    wherein the spot of illumination from the capture source is configured to be scanned over the tissue using the translational stage.

6. The system of claim 2, wherein the imaging system comprises an imaging light source optically coupled to the tissue,
    wherein the imaging system is configured to obtain images of the tissue using the imaging light source.

7. The system of claim 6, wherein the imaging system further comprises an objective lens optically coupled to the imaging light source and the capture source.

8. The system of claim 2, wherein the imaging system includes at least one of an optical coherence tomography (OCT) system, an optical coherence tomography (OCM) system, a spectrally encoded confocal microscopy (SECM) system, a fluorescence microscopy system, a confocal microscopy system, a structured illumination microscopy system, or a super-resolution microscopy system.

9. The system of claim 2, wherein the imaging system further comprises a detector configured to detect the images of the tissue.

10. The system of claim 2, wherein the imaging system comprises a benchtop microscopic imaging system, and
    wherein the tissue comprises an ex vivo tissue.

11. The system of claim 1, further comprising a tissue altering source optically coupled to the tissue by the optical system.

12. An apparatus for obtaining or treating at least one anatomical sample, comprising:
    a housing that is inserted into a body or provided on a hydrated anatomical structure,
        an outer surface of the housing comprising a capture material or a release material;
    an imaging system configured to obtain images of the at least one anatomical sample; and
    a source which is configured to emit light radiation to the capture material or a release material via the housing which causes at least one of:
        the at least one anatomical sample to attach to at least one portion of the housing, or
        release of a compound to the at least one anatomical sample from at least one portion of the housing.

13. The apparatus of claim 12, wherein the imaging system comprises an imaging light source optically coupled to the at least one anatomical sample,
    wherein the imaging system is configured to obtain images of the at least one anatomical sample using the imaging light source, and
    wherein the imaging light source is coupled to the imaging system by a rotary junction.

14. The apparatus of claim 13, wherein the rotary junction comprises achromatic optical elements.

15. An apparatus for obtaining or treating at least one anatomical sample, comprising:
    a housing that is inserted into a body or provided on a hydrated anatomical structure,
        an outer surface of the housing comprising a capture material or a release material; and
    a source which is configured to emit light radiation to the capture material or a release material via the housing which causes at least one of:
        the at least one anatomical sample to attach to at least one portion of the housing, or
        release of a compound to the at least one anatomical sample from at least one portion of the housing,
        wherein the capture material or the release material is coated onto a substrate.

16. The apparatus of claim 15, wherein the capture material or the release material is coated onto the substrate by dip-coating.

17. The apparatus of claim 15, wherein the capture material or the release material is coated onto the substrate by applying a stream of the capture material or the release material onto the substrate while the substrate is rotated,
- wherein a thickness of the capture material or the release material is based on a speed at which the substrate is rotated.

18. The apparatus of claim 15, wherein the capture material or the release material is coated onto the substrate by spraying the capture material or the release material onto the substrate while the substrate is rotated,
- wherein a thickness of the capture material or the release material is based on a speed at which the substrate is rotated.

19. The apparatus of claim 15, wherein the capture material or the release material is coated onto the substrate by applying a stream of the capture material or the release material onto a central portion of the substrate while the substrate is rotated,
- wherein a thickness of the capture material or the release material at a peripheral portion of the substrate is based on a speed at which the substrate is rotated.

20. The apparatus of claim 15, wherein the capture material or the release material is coated onto the substrate by melting the capture material or the release material onto the substrate.

* * * * *

UNITED STATES PATENT AND TRADEMARK OFFICE
CERTIFICATE OF CORRECTION

PATENT NO. : 11,864,743 B2
APPLICATION NO. : 17/168374
DATED : January 9, 2024
INVENTOR(S) : Guillermo J. Tearney et al.

Page 1 of 1

It is certified that error appears in the above-identified patent and that said Letters Patent is hereby corrected as shown below:

In the Specification

Column 1, Line 20, "EB022077" should be --NIH/EB022077--.

Signed and Sealed this
Third Day of June, 2025

Coke Morgan Stewart
*Acting Director of the United States Patent and Trademark Office*